US008107686B2

(12) United States Patent
Matsuda

(10) Patent No.: US 8,107,686 B2
(45) Date of Patent: Jan. 31, 2012

(54) IMAGE PROCESING APPARATUS AND IMAGE PROCESSING METHOD

(75) Inventor: Takehiro Matsuda, Hachioji (JP)

(73) Assignee: Olympus Corporation, Tokyo (JP)

( * ) Notice: Subject to any disclaimer, the term of this patent is extended or adjusted under 35 U.S.C. 154(b) by 881 days.

(21) Appl. No.: 12/166,520

(22) Filed: Jul. 2, 2008

(65) Prior Publication Data

US 2009/0010551 A1    Jan. 8, 2009

(30) Foreign Application Priority Data

Jul. 4, 2007    (JP) ................. 2007-176531

(51) Int. Cl.
 *G06K 9/00*    (2006.01)
 *G06K 9/46*    (2006.01)
(52) U.S. Cl. ................ 382/107; 382/224; 382/236
(58) Field of Classification Search .............. 382/103, 382/108, 128, 181, 197, 224, 236; 348/413.1, 348/416.1, 699; 375/240.16
 See application file for complete search history.

(56) References Cited

U.S. PATENT DOCUMENTS

| 2007/0165932 | A1 | 7/2007 | Nishimura et al. | |
| 2007/0195165 | A1 | 8/2007 | Hirakawa | |
| 2007/0268280 | A1* | 11/2007 | Fujita et al. | 345/204 |
| 2008/0130748 | A1* | 6/2008 | Robers et al. | 375/240.16 |

FOREIGN PATENT DOCUMENTS

| JP | 2006-280792 | 10/2006 |
| WO | WO 2006/123455 A1 | 11/2006 |
| WO | WO 2007/077672 A1 | 12/2007 |

* cited by examiner

*Primary Examiner* — Daniel Mariam
(74) *Attorney, Agent, or Firm* — Scully, Scott, Murphy & Presser, P.C.

(57) ABSTRACT

In an image processing apparatus which processes time-series images picked up by an imaging device in time series, a motion-vector calculating unit calculates a motion vector between plural images constituting the time-series images with respect to plural pixel regions set in the image. A newly-appearing-rate estimating unit estimates a newly-appearing rate which is a rate of a region newly appears in an image between plural images based on the motion vector. A display-time determination coefficient calculating unit calculates a display time of an image according to the newly-appearing rate.

34 Claims, 24 Drawing Sheets

101

103

105

111

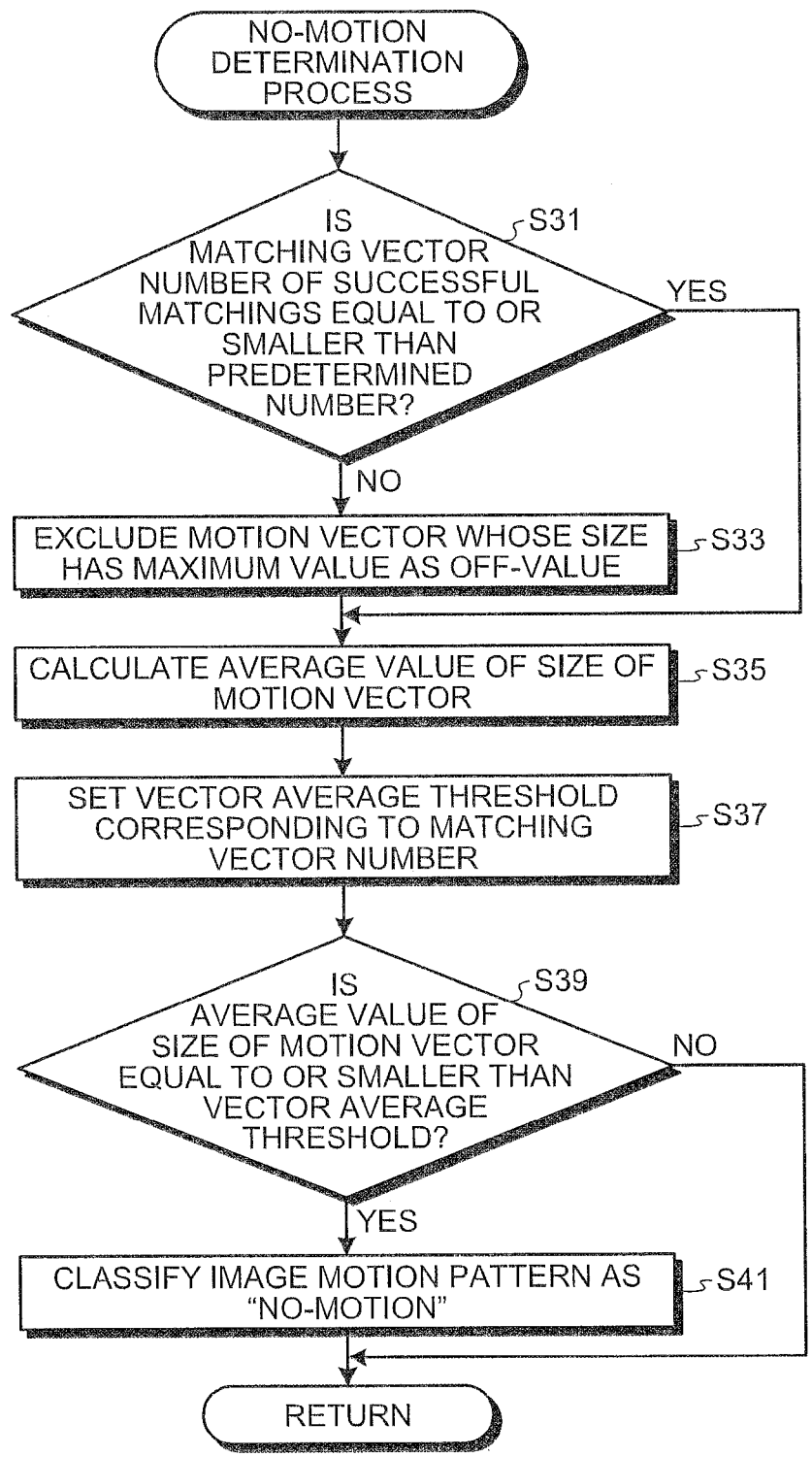

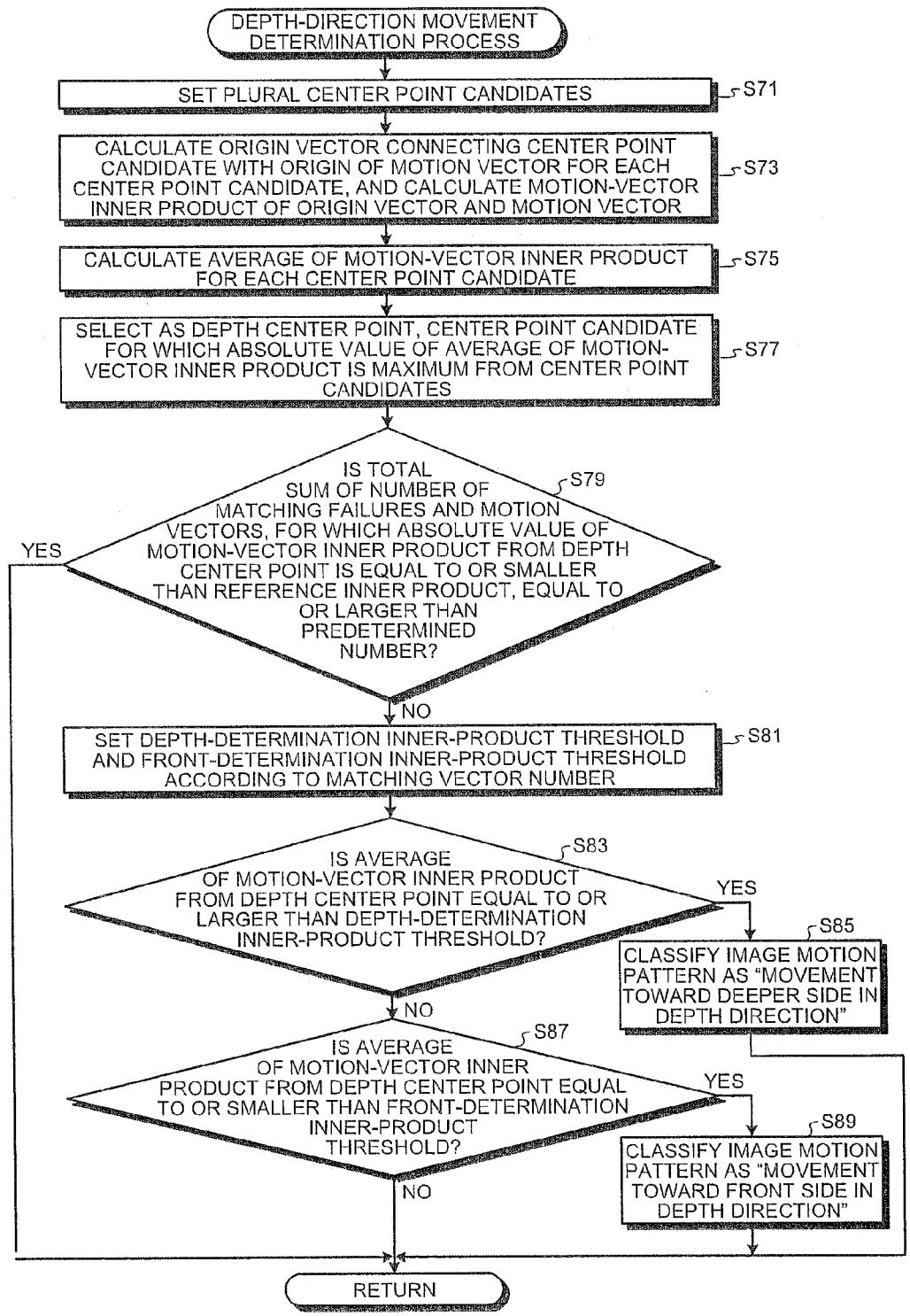

US 8,107,686 B2

IMAGE PROCESING APPARATUS AND IMAGE PROCESSING METHOD

CROSS-REFERENCE TO RELATED APPLICATIONS

This application is based upon and claims the benefit of priority from Japanese Patent Application No. 2007-176531, filed Jul. 4, 2007, the entire contents of which are incorporated herein by reference.

BACKGROUND OF THE INVENTION

1. Field of the Invention

The present invention relates to an image processing apparatus which processes time-series images obtained through image pickup along time series by an imaging device and an image processing method thereof.

2. Description of the Related Art

In recent years, in a field of endoscope, a swallowable capsule endoscope is proposed. The capsule endoscope has an imaging function for picking up (or taking) images inside a subject, a transmission function for radio transmitting image information obtained through image pickup by an imaging unit, and the like, and is configured with a capsule-like casing housing these functions. For the introduction of the capsule endoscope into a subject, a patient, i.e., the subject of an examination swallows the capsule endoscope from the mouth. The capsule endoscope travels through inside the subject body, e.g., through internal organs such as an esophagus, a stomach, a small intestine, and a large intestine following peristaltic movements thereof until naturally excreted from the body. While moving through inside the body, the capsule endoscope sequentially picks up images of the interior of the body at the rate of 2 to 4 frames/sec, for example, and radio transmits image information obtained through image pickup to a receiver outside the body. Images of the interior of the subject picked up by the capsule endoscope and received by the receiver outside the body are sequentially displayed on a diagnosis-dedicated workstation or the like in an order of time series, and checked by an observer such as a doctor.

The capsule endoscope picks up an enormous amount of images. Hence, the diagnosis-dedicated workstation or the like determines whether each image is worth observation or not based on a degree of similarity between adjacent images in time series. Then, the workstation or the like adjusts display time of each image by lengthening the display time of an image which is worth observation, and shortening the display time of an image which is not worth observation, so as to alleviate the burden of image observation on the observer. As one technique for the above, it is known to set plural pixel regions in an image, find a motion vector of each pixel region between images successive in time series, and determine a degree of similarly of the images. For example, according to one known technique, a motion vector of each pixel region is calculated with respect to successive images in time series; a motion vector with a largest motion vector amount (or length) is selected; and a display time of each image is calculated based on the motion vector amount (representative motion vector amount) of the selected motion vector. Further, according to another known technique, an image which shows an identical imaging scene with other image is found by checking whether each of calculated motion vectors are in the same direction or not, and an image which shows an identical imaging scene with other image which is adjacent thereto in time series is displayed for a short time period or is skipped (see Japanese Patent Application Laid-Open No. 2006-280792).

SUMMARY OF THE INVENTION

An image processing apparatus according to one aspect of the present invention processes time-series images picked up by an imaging device in time series, and includes a motion-vector calculating unit that calculates a motion vector between plural images constituting the time-series images with respect to plural pixel regions set in the image, a newly-appearing-rate estimating unit that estimates a newly-appearing rate, which is a rate of a newly-appeared region in an image between the plural images, based on a motion vector calculated by the motion-vector calculating unit, and a display-time calculating unit that calculates a display time of the image according to a newly-appearing rate estimated by the newly-appearing-rate estimating unit.

An image processing method according to another aspect of the present invention processes time-series images picked up by an imaging device in time series, and includes calculating a motion vector between plural images constituting the time-series images with respect to plural pixel regions set in the image, estimating a newly-appearing rate, which is a rate of a region newly appears in an image between the plural images, based on a motion vector calculated in the calculating, and calculating a display time of the image according to the newly-appearing rate estimated in the estimating.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 7 is a flowchart of process procedures of a no-motion determination process;

FIG. 13 is a flowchart of process procedures of a depth-direction movement determination process;

DETAILED DESCRIPTION OF THE PREFERRED EMBODIMENTS

Exemplary embodiments of the present invention are described in detail below with reference to the accompanying drawings.

Figure 1:
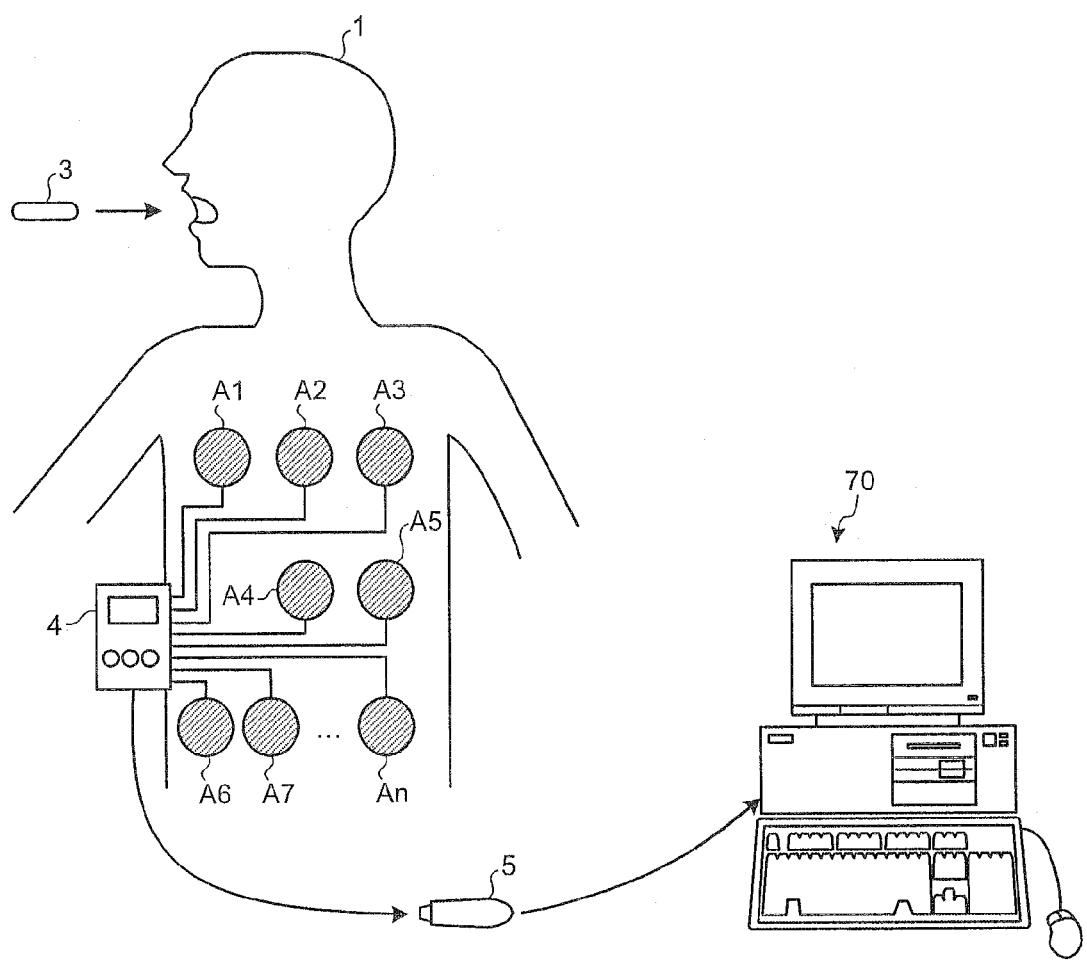
FIG. 1 is a schematic diagram of an overall configuration of an image processing system including an image processing apparatus according to an embodiment.

FIG. 1 is a schematic diagram of an overall configuration of an image processing system including an image processing apparatus according to an embodiment. The image processing apparatus of the embodiment is an image processing apparatus that processes and displays an image picked up by a capsule endoscope inside a body cavity. As shown in FIG. 1, the image processing system includes a capsule endoscope 3, a receiving apparatus 4, an image processing apparatus 70, and the like. The capsule endoscope 3 picks up an image (intra-body image) inside a subject 1. The receiving apparatus 4 receives an intra-body image radio transmitted by the capsule endoscope 3. The image processing apparatus 70 processes and displays the intra-body image picked up by the capsule endoscope 3 based on the intra-body image received by the receiving apparatus 4. Image data is transferred between the receiving apparatus 4 and the image processing apparatus 70 with the use of a recording medium of a portable type (portable recording medium) 5, for example.

The capsule endoscope 3 has an imaging function, a radio communication function, and the like, and is swallowed by the subject 1 from the mouth for the introduction into the subject 1, and sequentially picks up intra-body images while traveling through body cavities. Then, the capsule endoscope 3 radio transmits the picked-up intra-body images to an outside of the body.

The receiving apparatus 4 has plural receiving antennas A1 to An, to receive the intra-body image radio transmitted by the capsule endoscope 3 via the respective receiving antennas A1 to An. The receiving apparatus 4 is so configured that the portable recording medium 5 can be attached/detached thereto/therefrom so as to sequentially store image data of the received intra-body image in the portable recording medium 5. Thus, the receiving apparatus 4 accumulates intra-body images picked up by the capsule endoscope 3 inside the subject 1 in the portable recording medium 5 in an order of time series.

The receiving antennas A1 to An are configured with, for example, loop antennas, and are distributively arranged at predetermined positions on a body surface of the subject 1 as shown in FIG. 1. Specifically, the receiving antennas A1 to An are distributively arranged on the body surface at positions corresponding to the travelling route of the capsule endoscope 3 in the subject 1, for example. The receiving antennas A1 to An may be distributively arranged on a jacket the subject 1 wears. Then, when the subject 1 wears the jacket, the receiving antennas A1 to An are arranged on the body surface of the subject 1 at predetermined positions corresponding to the travelling route of the capsule endoscope 3 in the subject. As far as one or more receiving antennas are arranged for each subject 1, the number of the receiving antennas is not limited.

The image processing apparatus 70 is realized with a general computer such as a workstation and a personal computer, and is so configured that the portable recording medium 5 is attachable/detachable thereto/therefrom. The image processing apparatus 70 acquires intra-body images in time series as accumulated in the portable recording medium 5 and successively displays the time-series intra-body images as acquired on a display such as an LCD or an ELD by sequentially switching from one image to another.

Figure 2:
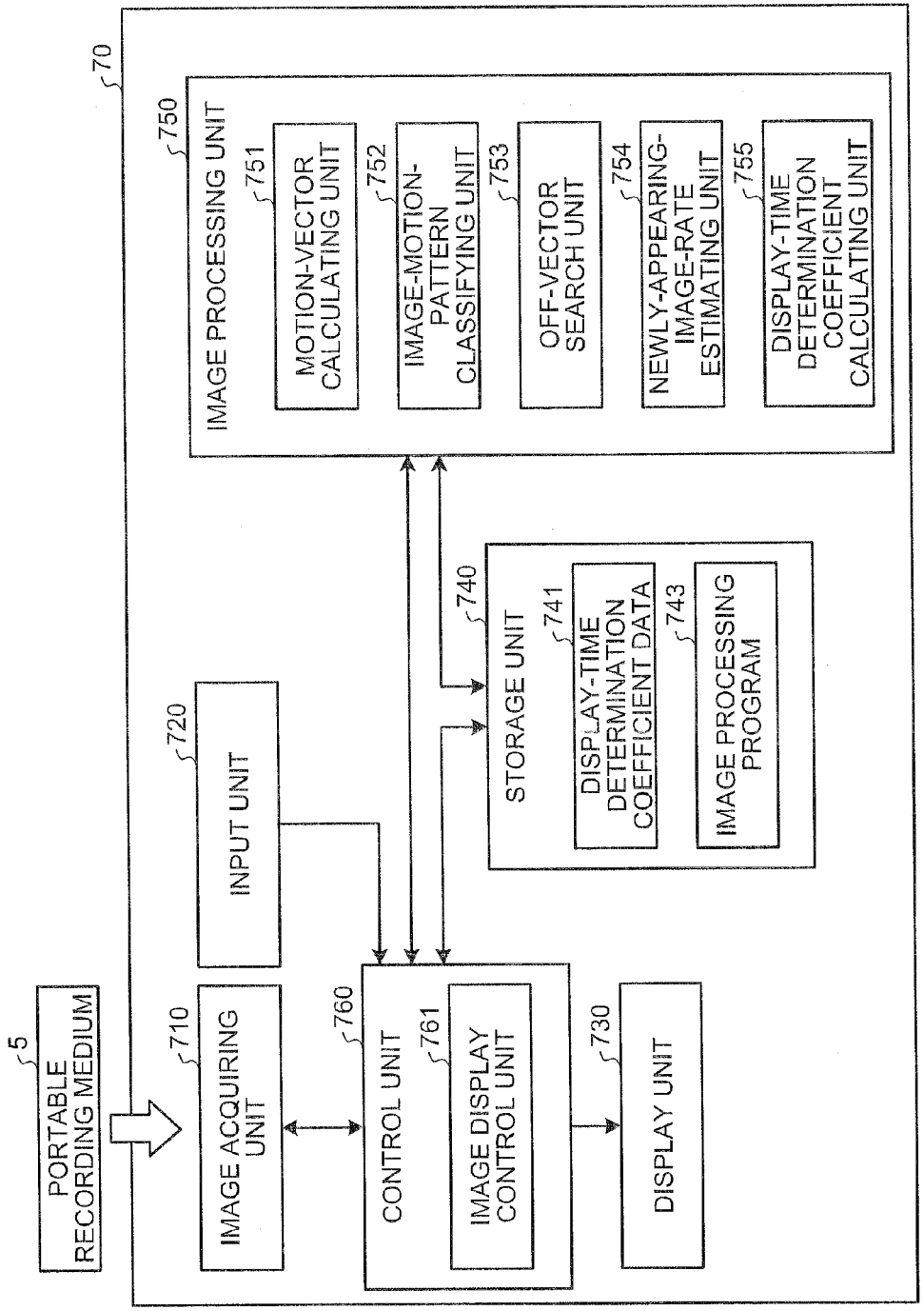
FIG. 2 is a block diagram for explaining a functional configuration of the image processing apparatus.

FIG. 2 is a block diagram for explaining a functional configuration of the image processing apparatus 70. In the embodiment, the image processing apparatus 70 includes an image acquiring unit 710, an input unit 720, a display unit 730, a storage unit 740, an image processing unit 750, and a control unit 760 which controls each unit of the apparatus.

The image acquiring unit 710 acquires time-series intra-body images as picked up by the capsule endoscope 3. For example, the portable recording medium 5 is detachably attached to the image acquiring unit 710, and the image acquiring unit 710 reads out and thus acquires the image data of the time-series intra-body images accumulated in the attached portable recording medium 5. The image acquiring unit 710 is realized, for example, with a reader/writer compatible with the type of the portable recording medium 5. The acquisition of the time-series intra-body images picked up by the capsule endoscope 3 is not limited to the acquisition with the use of the portable recording medium 5. For example, a hard disk may be provided in place of the image acquiring unit 710, so that the time-series intra-body images picked up by the capsule endoscope 3 are stored in the hard disk in advance. Alternatively, a separate server may be provided in place of the portable recording medium 5, so that the time-series intra-body images are stored in the server in advance. In this case, the image acquiring unit 710 is configured with a communication device or the like so as to be connected to the server, and the apparatus is connected to the server via the image acquiring unit 710 so as to acquire the time-series intra-body images from the server.

The input unit 720 is realized, for example, with a keyboard, a mouse, a touch panel, various types of switches, or the like, to output an operation signal corresponding to an operation input to the control unit 760. The display unit 730 is realized with a display device such as an LCD and an ELD, to display various types of screens including a display screen of a time-series intra-body image under the control of the control unit 760.

The image processing unit 750 is realized with a hardware such as a CPU. The image processing unit 750 processes plural intra-body images, which are time-series images acquired by the image acquiring unit 710, and performs various types of arithmetic processes to calculate a display-time determination coefficient for determining a display time of the display of each intra-body image on the display unit 730. The image processing unit 750 includes a motion-vector calculating unit 751, an image-motion-pattern classifying unit 752, an off-vector search unit 753, a newly-appearing-image-rate estimating unit 754, and a display-time determination coefficient calculating unit 755. The image-motion-pattern classifying unit 752 can be referred to as a motion-pattern classifying unit. The off-vector search unit 753 can be referred to as an off-pattern-vector extracting unit. The newly-appearing-image-rate estimating unit 754 can be referred to as a newly-appearing-rate estimating unit. The display-time determination coefficient calculating unit 755 can be referred to as a display-time calculating unit. The motion-vector calculating unit 751 associates an identical object appears in different intra-body images with each other to calculate vector data (motion vector) representing the amount of change of the position of the object. The image-motion-pattern classifying unit 752 classifies a motion pattern of each intra-body image (hereinafter referred to as "image motion pattern"), in other words, a motion pattern of the capsule endoscope 3 at the time of image pickup of each intra-body image. Specifically, the image-motion-pattern classifying unit 752 classifies as one of image motion patterns including "no-motion", "parallel movement", "movement toward deeper side in depth direction", "movement toward front side in depth direction", and "scene change" based on the motion vector. The off-vector search unit 753 searches the motion vectors of each intra-body image for a motion vector which is off from the image motion pattern of the intra-body image and extracts the found vector as an off-vector. The newly-appearing-image-rate estimating unit 754 estimates a region which does not exist in a former time-series image and newly appears in a pertinent intra-body image (hereinafter referred to as "newly-appeared region") for each intra-body image, and calculates the rate of the newly-appeared region as a newly-appearing rate. The display-time determination coefficient calculating unit 755 calculates a display-time determination coefficient which is a calculation parameter for determining a display time of each intra-body image based on the newly-appearing rate.

The control unit 760 is realized with a hardware such as a CPU. The control unit 760 transfers, for example, the image data of the intra-body image supplied from the image acquiring unit 710, operation signals supplied from the input unit 720, and an instruction and data to each unit constituting the image processing apparatus 70 according to a program, data, and the like stored in the storage unit 740. The control unit 760 thus controls an operation of the image processing apparatus 70 as a whole in an integrated manner. Further, the control unit 760 includes an image display control unit 761 which controls the display of the time-series intra-body images supplied by the image acquiring unit 710 so that the time-series intra-body images are sequentially displayed in an order of time series on the display unit 730 for a display time of each.

The storage unit 740 is realized, for example, with an IC memory of various types, such as a store-updatable flash memory, a ROM, and a RAM, a hard disk which is embedded or connected via a data communication terminal, an information recording medium such as a CD-ROM and a reader device of the medium, and the like. The storage unit 740 stores therein a program related with the operation of the image processing apparatus 70, a program for realizing various types of functions of the image processing apparatus 70, data related with the execution of these programs, and the like. Further, the storage unit 740 stores display-time determination coefficient data 741 in which a display-time determination coefficient of each intra-body image calculated by the display-time determination coefficient calculating unit 755 is stored. The data of the display-time determination coefficient may be written into the portable recording medium 5 in association with each intra-body image. Further, the storage unit 740 stores therein an image processing program 743 for making the image processing unit 750 work as the motion-vector calculating unit 751, the image-motion-pattern classifying unit 752, the off-vector search unit 753, the newly-appearing-image-rate estimating unit 754, and the display-time determination coefficient calculating unit 755.

Figure 3:
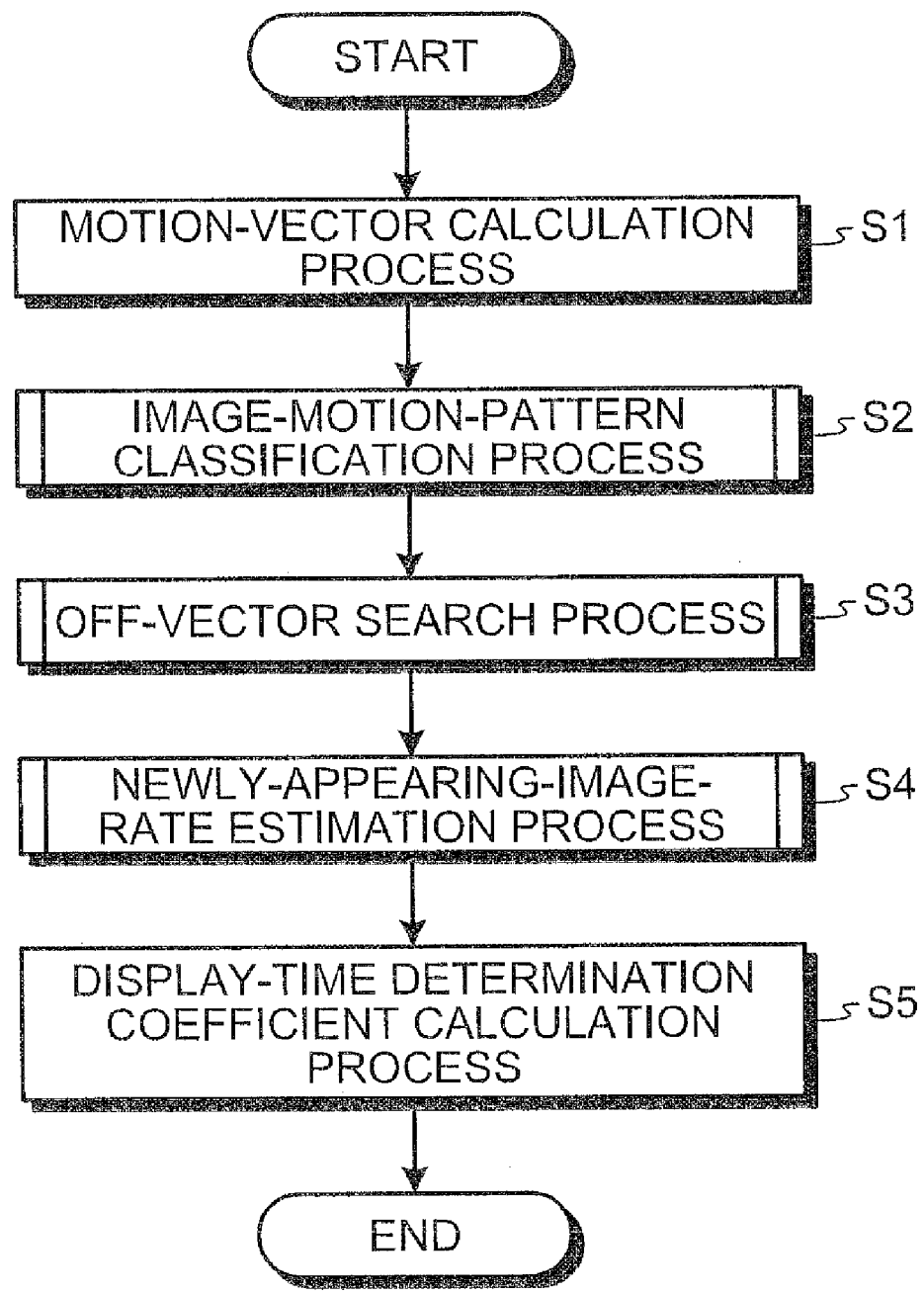
FIG. 3 is an overall flowchart of process procedures performed by the image processing apparatus.

FIG. 3 is an overall flowchart of process procedures performed by the image processing apparatus 70. The processes described here are realized when the image processing unit 750 reads out and executes the image processing program 743 stored in the storage unit 740.

As shown in FIG. 3, firstly, the motion-vector calculating unit 751 performs a motion-vector calculation process (step S1). Then, the image-motion-pattern classifying unit 752 performs an image-motion-pattern classification process (step S2). Subsequently, the off-vector search unit 753 performs an off-vector search process (step S3). Then, the newly-appearing-image-rate estimating unit 754 performs a newly-appearing-image-rate estimation process (step S4). Then, the display-time determination coefficient calculating unit 755 performs a display-time determination coefficient calculation process (step S5). Through the processes of steps S1 to S5, the display-time determination coefficient of each intra-body image is obtained. After these processes, the image display control unit 761 controls so that the intra-body images are sequentially displayed on the display unit 730 in an order of time series each for a display time determined by the display-time determination coefficient. Here, the process for calculating the display-time determination coefficient of each intra-body image may be performed in the image processing apparatus, and the intra-body images may be sequentially displayed in an order of time series each for a display time determined by the display-time determination coefficient on an apparatus separate from the image processing apparatus. Details of the processes performed in steps S1 to S5 are described below with a focus on how the display-time determination coefficient of one intra-body image (hereinafter referred to as "process target image" as appropriate) is found.

Firstly, the motion-vector calculation process in step S1 of FIG. 3 is described. In the motion-vector calculation process, the motion-vector calculating unit 751 performs template matching using plural pixel regions set in the intra-body image as templates. Then, the motion-vector calculating unit 751 calculates a motion vector of each template position relative to the intra-body image which is acquired before in the time series (hereinafter referred to as "former time-series image" as appropriate), for example.

Figure 4A:
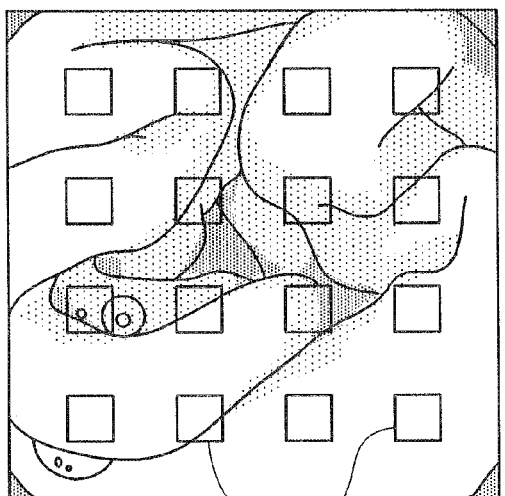
FIG. 4A is a view of an example of a former time-series image.
Figure 4B:
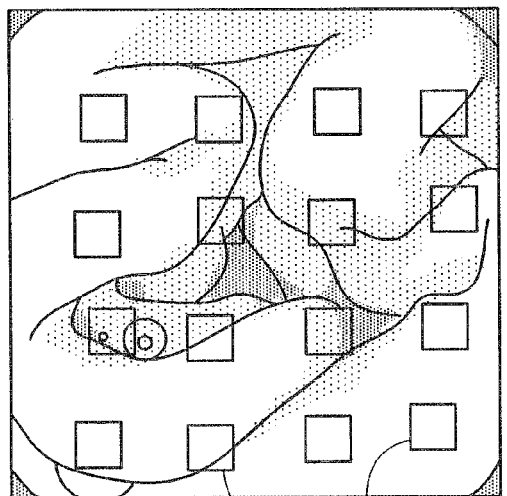
FIG. 4B is a view of an example of a process target image.
Figure 4C:
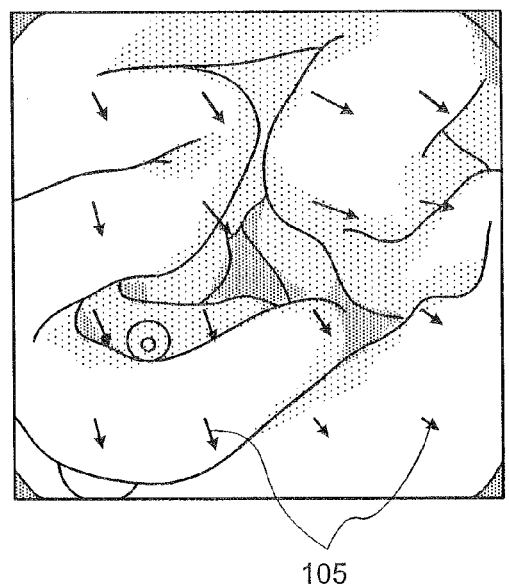
FIG. 4C is a view in which motion vectors calculated based on the former time-series image of FIG. 4A and the process target image of FIG. 4B are shown in the process target image.

FIG. 4A is a view of an example of the former time-series image, FIG. 4B is a view of an example of the process target image, and FIG. 4C is a view of motion vectors in the process target image calculated based on the former time-series image of FIG. 4A and the process target image of FIG. 4B. The motion-vector calculating unit 751 first sets pixel regions 101 of a predetermined number (16, for example) in the former time-series image as shown in FIG. 4A. The position, size, number, and the like of the pixel regions to be set may be previously determined, or configured to be settable and changeable according to a user operation or the like. Subsequently, the motion-vector calculating unit 751 sequentially uses each pixel region 101 as a template to perform a known template matching process, and searches for a position which matches with the template to a highest degree (in other words, a position with a high correlation value) in the process target image. As a technique of template matching, matching based on normalization cross-correlation is employed, for example. More specifically, for higher-speed processing, a technique of multi-resolution pyramid search is employed, according to which a matching region is sequentially searched from a low-resolution image and a search range is narrowed down. Here, the motion-vector calculating unit 751 calculates an average pixel value of each pixel region in the former time-series image employed as a template, and does not perform template matching for a dark pixel region whose average pixel value is not higher than a predetermined threshold, and treats the matching of this region as failure. Similarly, when the matching region cannot be found in the course of matching search based on the multi-resolution pyramid search, or when the obtained correlation value is low, the motion-vector calculating unit 751 treats the process as matching failure. As a result of template matching, template positions 103 which are most similar to respective pixel regions 101 of FIG. 4A are found from the process target image as shown in FIG. 4B, and the correlation values thereof are found. Then, the motion-vector calculating unit 751, as shown in FIG. 4C, calculates motion vectors 105 based on the found template positions 103, or more specifically, template positions 103 found as a result of search and for which the matching is successful. Data on the result of matching obtained through the motion-vector calculation process is stored in the storage unit 740. For example, failure or success of the matching, an obtained template position, a correlation value of the obtained template position, a motion vector, and the like are stored in association with an identification number of a pixel region employed as a template.

Figure 5:
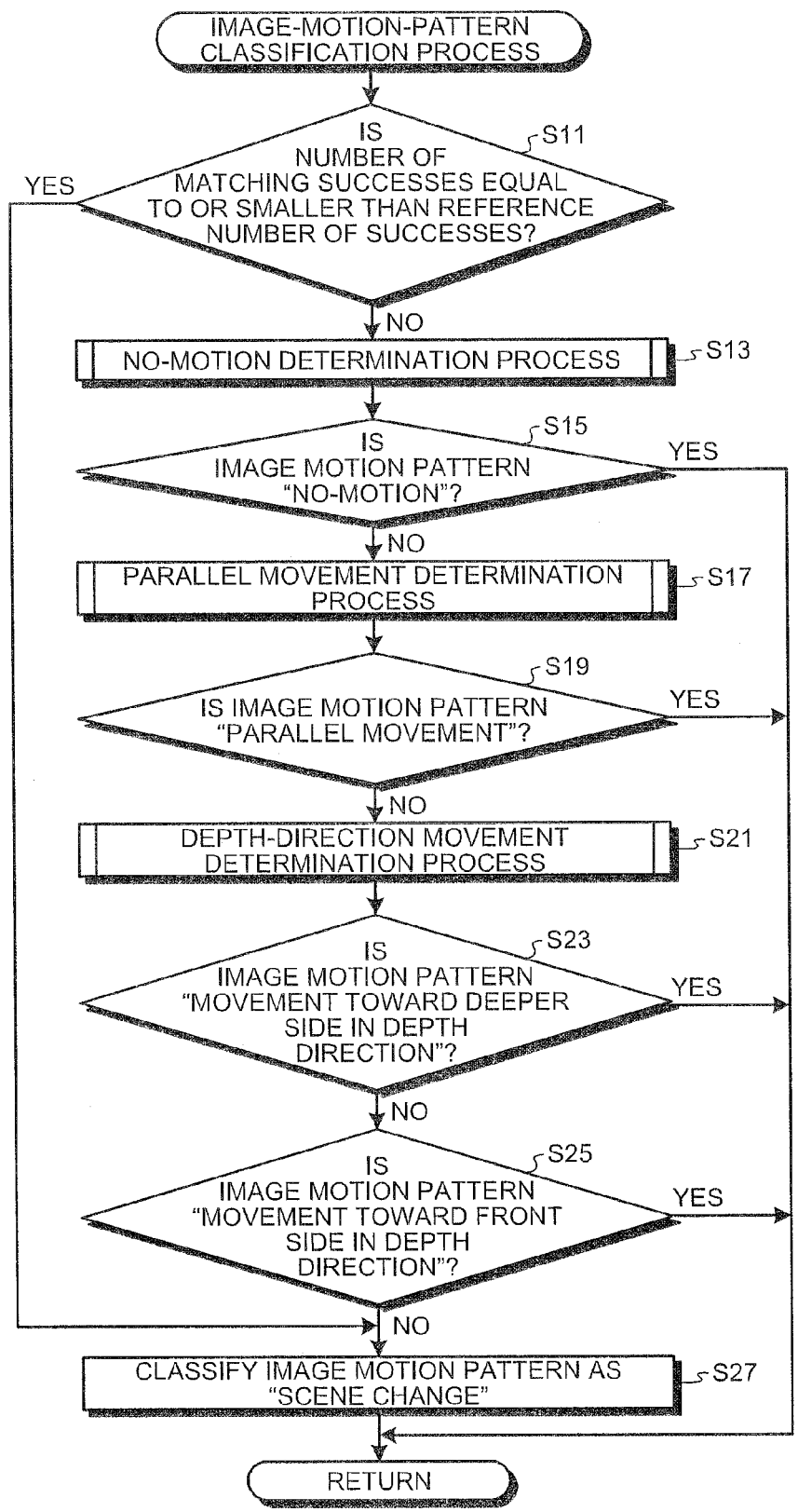
FIG. 5 is a flowchart of detailed process procedures of an image-motion-pattern classification process.

The image-motion-pattern classification process in step S2 of FIG. 3 is described. FIG. 5 is a flowchart of detailed process procedures of the image-motion-pattern classification process.

Figure 6A:
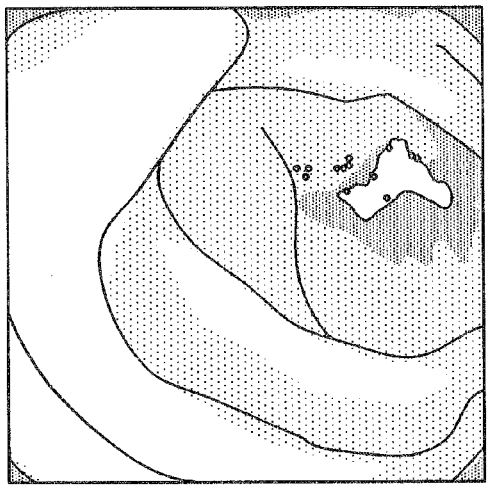
FIG. 6A is a view of an example of the former time-series image.
Figure 6B:
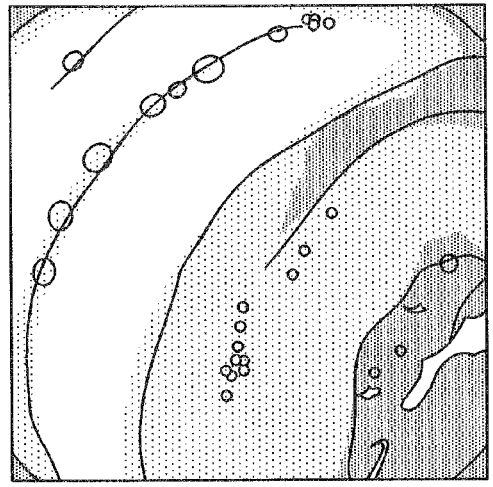
FIG. 6B is a view of an example of the process target image.
Figure 6C:
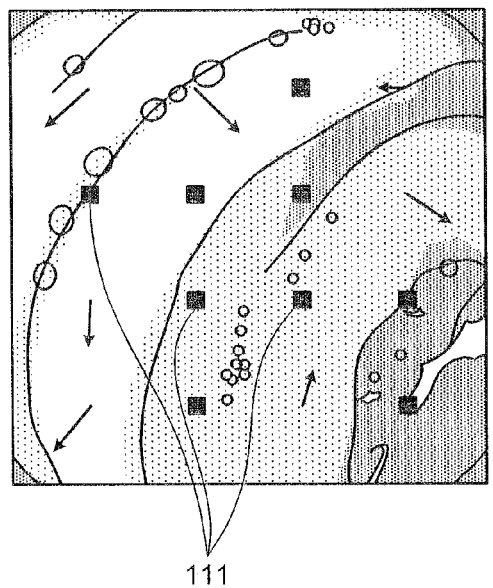
FIG. 6C is a view in which motion vectors calculated based on the former time-series image of FIG. 6A and the process target image of FIG. 6B are shown in the process target image.

In the image-motion-pattern classification process, the image-motion-pattern classifying unit 752 first compares the number of matching successes in the motion-vector calculation process which is an example of a confidence value and a reference number of successes previously set as a threshold. Then, when the number of matching successes is equal to or smaller than the reference number of successes (Yes in step S11), the image-motion-pattern classifying unit 752 proceeds to step S27 and classifies the pertinent image motion pattern as "scene change". FIG. 6A is a view of an example of the former time-series image, FIG. 6B is a view of an example of the process target image, and FIG. 6C is a view of motion vectors in the process target image calculated based on the former time-series image of FIG. 6A and the process target image of FIG. 6 11 As in the former time-series image and the process target image shown, when the imaging position of the capsule endoscope 3 changes significantly before and after a point in time series and an appearance of the image changes significantly, a position which matches with the template set in the former time-series image cannot be found in the process target image. Otherwise, the correlation value at the obtained template matching position is low. Then, the matching fails at many positions 111 as shown in FIG. 6C. When the number of templates for which the matching succeeds is not larger than the reference number of successes, the image motion pattern is classified as "scene change".

On the other hand, when the number of matching successes is larger than the reference number of successes (No in step S11), the image-motion-pattern classifying unit 752 performs a no-motion determination process (step S13) as shown in FIG. 5.

FIG. 7 is a flowchart of process procedures of the no-motion determination process. In the no-motion determination process, the image-motion-pattern classifying unit 752 first determines whether the number of vectors obtained as a result of successful matching (i.e., matching vector number) is equal to or smaller than a predetermined number previously set as a threshold for determination in step S31. When the matching vector number is larger than the predetermined number (No in step S31), the image-motion-pattern classifying unit 752 selects a motion vector which has a maximum size and excludes the same as an off-value from process target subsequent to step S35 (step S33). In the motion vector calculation process, the motion vector is sometimes obtained at an incorrect matching position. The above technique takes such a motion vector into consideration to enhance determination accuracy. However, when the number of motion vectors for which the matching is successful is small, the exclusion of off-value which reduces the number of motion vectors to be employed for the determination of image motion pattern may cause the erroneous classification of the image motion pattern. Hence, when the matching vector number is equal to or smaller than the predetermined number (Yes in step S31), the off-value exclusion process of step S33 is not performed.

Figure 8:
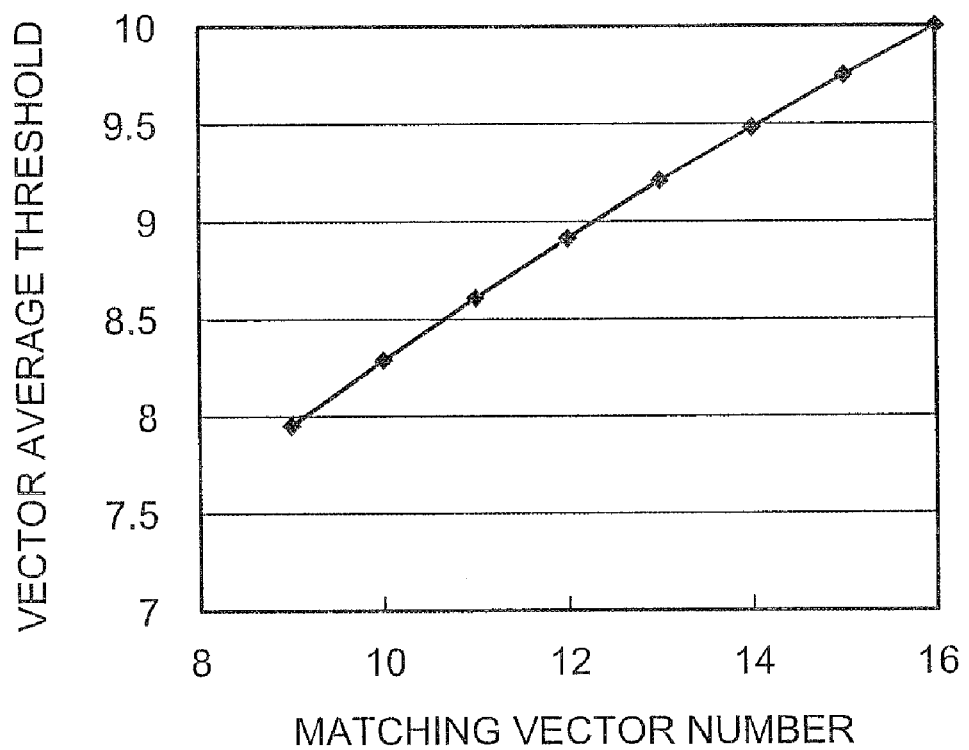
FIG. 8 is a graph of an example of vector average threshold.

Subsequently, the image-motion-pattern classifying unit 752 calculates an average value of the size of the motion vector based on the motion vectors other than the motion vector excluded as the off-value (step S35). Then, the image-motion-pattern classifying unit 752 sets a vector average threshold corresponding to the matching vector number (step S37). FIG. 8 is a graph for explaining how the vector average threshold is set, where a horizontal axis represents the matching vector number and a vertical axis represents the vector average threshold, and an example of the vector average threshold set corresponding to the matching vector number is shown. As shown in FIG. 8, the vector average threshold is set so that the threshold becomes smaller as the matching vector number decreases. This is because, when the number of motion vectors employed for the no-motion determination is small, it becomes more likely that the image motion pattern of the process target image accidentally falls into the category of "no-motion".

In practice, the vector average threshold is calculated according to following equation (1) based on a reference vector average threshold previously set. In the equation (1), $V_s'$ represents the vector average threshold, $V_s$ represents the reference vector average threshold, p represents the number of motion vectors for which the matching is successful (i.e., matching vector number), N represents the number of motion vectors when all the matching are successful (N corresponds to the number of pixel regions set in the former time-series image), and $\alpha_s$ represents conversion coefficient.

$$V_s' = V_s \times \left(\frac{p}{N}\right)^{\alpha_s} \quad (1)$$

Figure 9A:
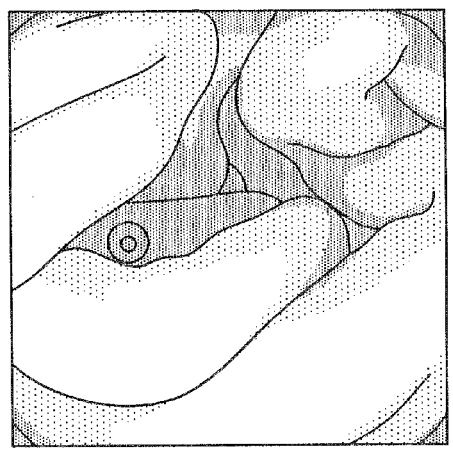
FIG. 9A is a view of an example of the former time-series image.
Figure 9B:
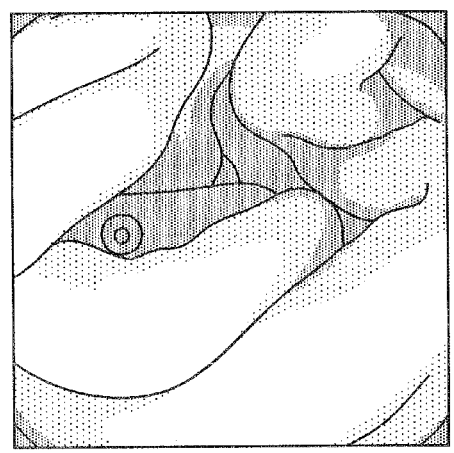
FIG. 9B is a view of an example of the process target image.
Figure 9C:
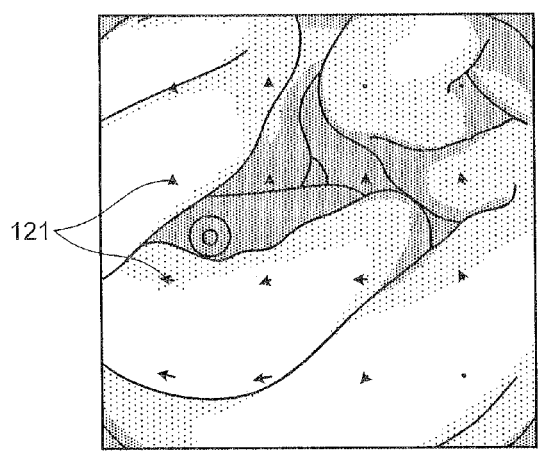
FIG. 9C is a view in which motion vectors calculated based on the former time-series image of FIG. 9A and the process target image of FIG. 9B are shown in the process target image.

Then, the image-motion-pattern classifying unit 752 determines on the average value of the size of the motion vector calculated in step S35 as shown in FIG. 7. When the average value of the size of the motion vector is equal to or smaller than the vector average threshold set in step S37 (Yes in step S39), the image-motion-pattern classifying unit 752 classifies the image motion pattern of the process target image as "no-motion" (step S41). In the embodiment, the image motion pattern of the process target image is classified as "no-motion" when the average value of the size of the motion vector calculated in step S35 is equal to or smaller than the vector average threshold set in step S37, though the manner of classification is not limited thereto. For example, such configuration is possible in which at least one of values including the average value, minimum value, maximum value, and intermediate value of the size of the vector is compared with a set threshold, and the image motion pattern of the process target image is classified as "no-motion" depending on the result of comparison. FIG. 9A is a view of an example of the former time-series image, FIG. 9B is a view of an example of the process target image, and FIG. 9C is a view of motion vectors in the process target image calculated based on the former time-series image of FIG. 9A and the process target image of FIG. 9B. When there is little change between images as in the former time-series image of FIG. 9A and the process target image of FIG. 9B, motion vectors 121 calculated based on the process target image as shown in FIG. 9C are small and the image motion pattern is classified as "no-motion". Thereafter, the image-motion-pattern classifying unit 752 returns to step S13 of FIG. 5 and proceeds to step S15.

In step S15, the image-motion-pattern classifying unit 752 determines whether the image motion pattern is "no-motion" or not. When the image motion pattern is classified as "no-motion" as a result of the no-motion determination process in step S13 (Yes in step S15), the image-motion-pattern classifying unit 752 finishes the process. On the other hand, when the image motion pattern is not "no-motion" (No in step S15), the image-motion-pattern classifying unit 752 performs a parallel movement determination process (step S17).

Figure 10:
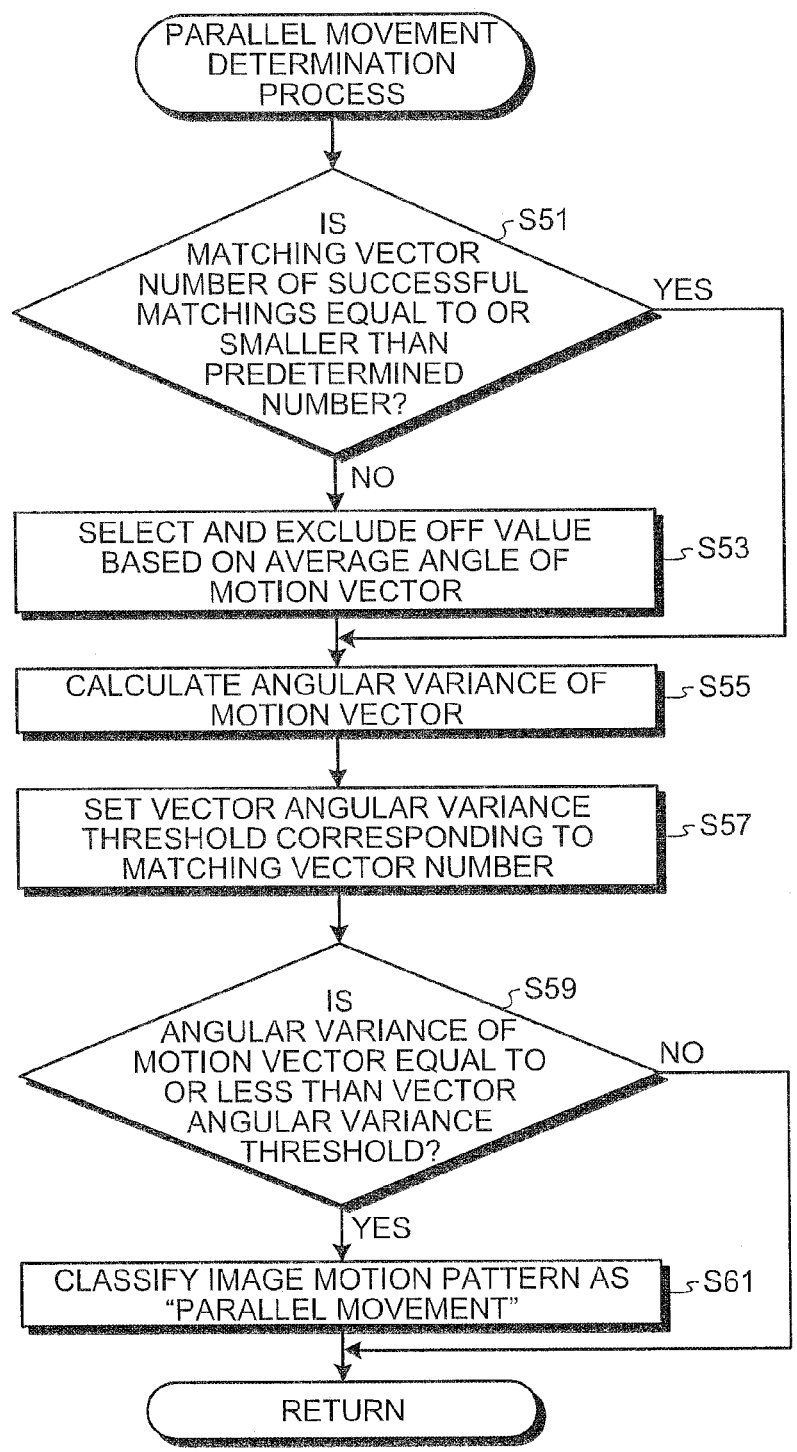
FIG. 10 is a flowchart of process procedures of a parallel movement determination process.

FIG. 10 is a flowchart of process procedures of the parallel movement determination process. When the image motion pattern of the intra-body image is "parallel movement", all the motion vectors have similar size and direction. In the parallel movement determination process, it is determined whether the image motion pattern is "parallel movement" or not based on the direction of each motion vector. Specifically, the image-motion-pattern classifying unit 752 first determines whether the matching vector number is equal to or smaller than a predetermined value previously set as a threshold for the determination in step S51. Then, when the matching vector number is larger than the predetermined value (No in step S51), the image-motion-pattern classifying unit 752 calculates the average of the angle (direction) of the motion vector to select a motion vector for which the absolute value of difference from the average angle is the largest. Then, the image-motion-pattern classifying unit 752 excludes the selected vector as an off-value from process target of step S55 and subsequent steps (step S53). This process, similarly to the no-motion determination process, aims at enhancing the determination accuracy by taking into consideration a case where the matching is performed at an incorrect position at the time of motion vector calculation. Hence, when the matching vector number of successful matching is equal to or smaller than the predetermined number (Yes in step S51), the off-value exclusion process of step S53 is not performed.

Figure 11:
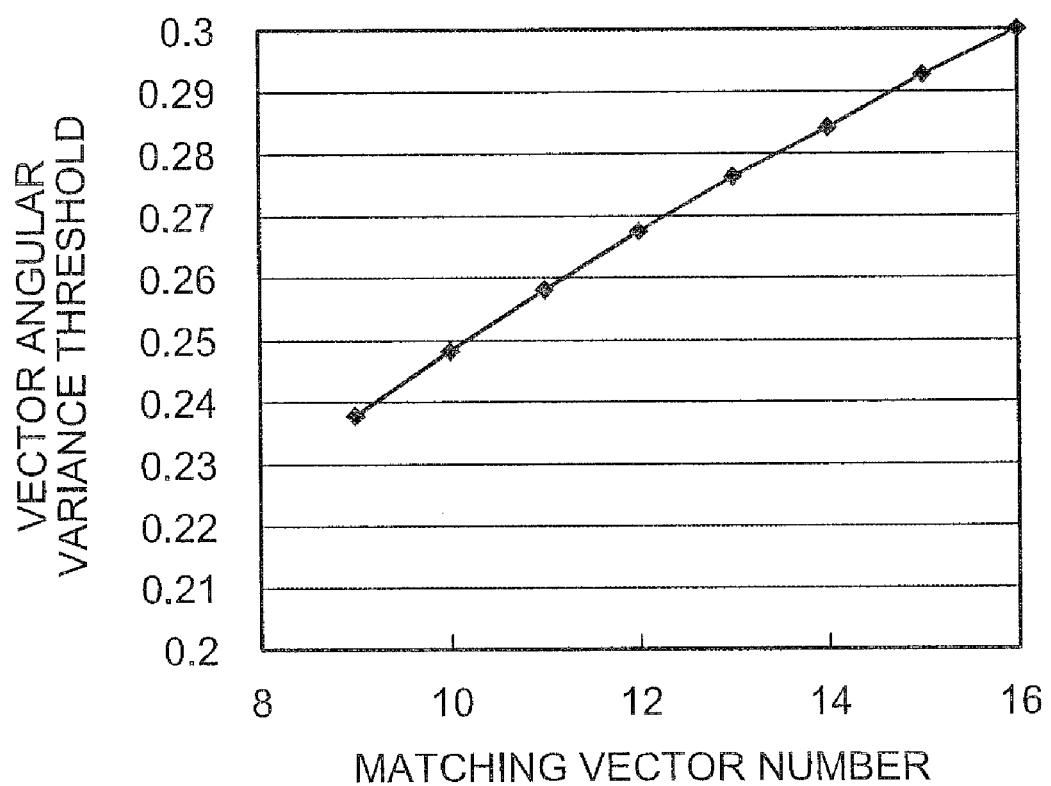
FIG. 11 is a graph of an example of vector angular variance threshold.

Subsequently, the image-motion-pattern classifying unit 752 calculates fluctuation of the angle of the motion vector based on the motion vectors other than the motion vector excluded as the off-value (step S55). In the embodiment, angular variance is calculated as the fluctuation of the angle. Then, the image-motion-pattern classifying unit 752 sets a vector angular variance threshold corresponding to the matching vector number (step S57). FIG. 11 is a graph for explaining how the vector angular variance threshold is set, where a horizontal axis represents the matching vector number and a vertical axis represents the vector angular variance threshold, and an example of the vector angular variance threshold set corresponding to the matching vector number is shown. As shown in FIG. 11, the vector angular variance threshold is set so that the threshold becomes smaller as the matching vector number decreases. This is because when the number of motion vectors employed for the parallel movement determination is small, it becomes more likely that the image motion pattern of the process target image accidentally falls into the category of "parallel movement".

In practice, the vector angular variance threshold is calculated according to following equation (2) based on a reference vector angular variance threshold previously set. Here, $V_p'$ represents the vector angular variance threshold, $V_p$ represents the reference vector angular variance threshold, p represents the number of motion vectors for which the matching is successful, N represents the number of motion vectors when all matching is successful, and $\alpha_p$ represents conversion coefficient.

$$V_p' = V_p \times \left(\frac{p}{N}\right)^{\alpha_p} \quad (2)$$

Figure 12A:
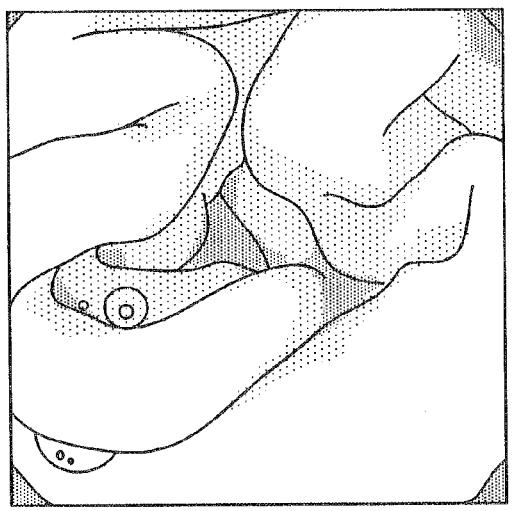
FIG. 12A is a view of an example of the former time-series image.
Figure 12B:
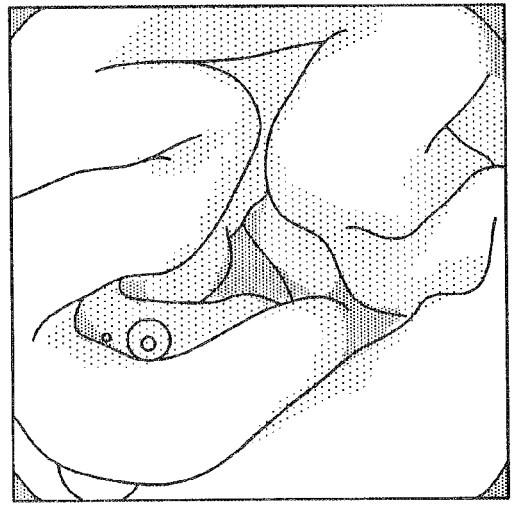
FIG. 12B is a view of an example of the process target image.
Figure 12C:
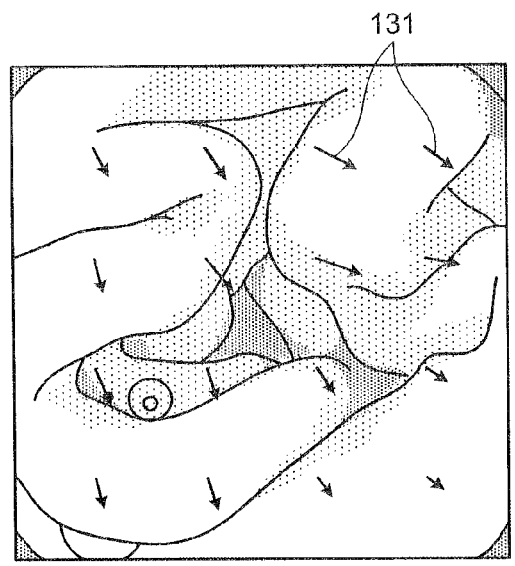
FIG. 12C is a view in which motion vectors calculated based on the former time-series image of FIG. 12A and the process target image of FIG. 12B are shown in the process target image.

Then, the image-motion-pattern classifying unit 752 determines on the angular variance of the motion vector calculated in step S55 as shown in FIG. 10. When the angular variance of the motion vector is equal to or smaller than the vector angular variance threshold set in step S57 (Yes in step S59), the image-motion-pattern classifying unit 752 classifies the image motion pattern of the process target image as "parallel movement" (step S61). FIG. 12A is a view of an example of the former time-series image, FIG. 12B is a view of an example of the process target image, and FIG. 12C is a view of motion vectors in the process target image calculated based on the former time-series image of FIG. 12A and the process target image of FIG. 12B. As shown in FIG. 12C, when the motion vectors 131 in the process target image as calculated based on the former time-series image of FIG. 12A and the process target image of FIG. 12B are directed substantially in the same direction, the image motion pattern is classified as "parallel movement". Then, the image-motion-pattern classifying unit 752 returns to step S17 of FIG. 5 and proceeds to step S19.

In step S19, the image-motion-pattern classifying unit 752 determines whether the image motion pattern is "parallel movement" or not. When the image motion pattern is "parallel movement", in other words, when the image motion pattern is classified as "parallel movement" as a result of the parallel movement determination process in step S17 (Yes in step S19), the image-motion-pattern classifying unit 752 finishes the process. On the other hand, when the image motion pattern is not "parallel movement" (No in step S19), the image-motion-pattern classifying unit 752 performs a depth-direction movement determination process (step S21).

Figure 14:
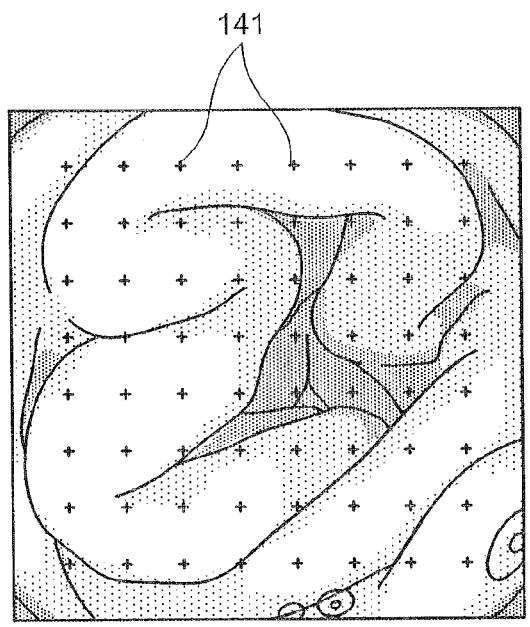
FIG. 14 is a view of an example of center point candidates set in the process target image.

FIG. 13 is a flowchart of process procedures of the depth-direction movement determination process. In the depth-direction movement determination process, the image-motion-pattern classifying unit 752 first sets a predetermined number of center point candidates in the process target image (step S71). FIG. 14 is a view of an example of center point candidates set in the process target image, wherein plural center point candidates 141 are arranged and set in the process target image. The position of each of the center point candidates 141 and the number thereof are previously set. The image-motion-pattern classifying unit 752 selects a depth center point from the center point candidates 141. Here, the depth center point corresponds to a point which indicates a destination of the capsule endoscope 3 in the image, in other words, an advancing-direction position which is a position where the advancing direction of the movement of the capsule endoscope 3 appears in the image. The image-motion-pattern classifying unit 752 selects the center point candidate 141 which is closest to the advancing-direction position of the capsule endoscope 3 in the process target image, and sets the selected point as the depth center point.

Specifically, the image-motion-pattern classifying unit 752 calculates a vector connecting the center point candidate with an origin of each motion vector for each of the center point candidates (hereinafter, such vector is referred to as "origin vector"). Subsequently, the image-motion-pattern classifying unit 752 calculates an inner product of each origin vector calculated with respect to each center point candidate and a motion vector whose origin is an end point of the origin vector (hereinafter referred to as "motion-vector inner product") (step S73). Then, the image-motion-pattern classifying unit 752 calculates the average of the motion-vector inner product for each center point candidate (step S75), and selects as the depth center point, a center point candidate for which the absolute value of the calculated average of the motion-vector inner product is maximum (step S77).

Figure 15A:
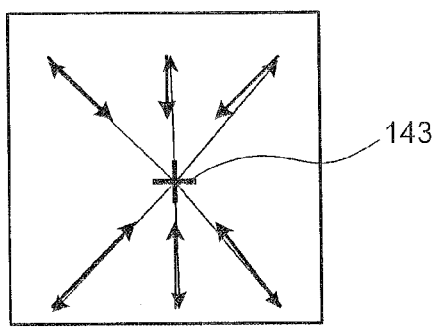
FIG. 15A is an explanatory diagram for explaining how depth center point is selected.
Figure 15B:
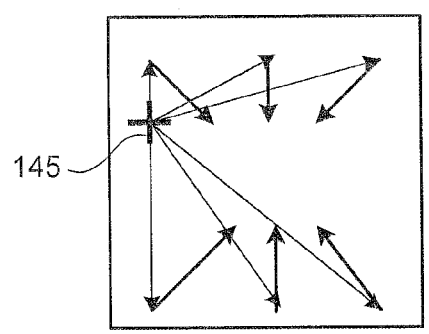
FIG. 15B is another explanatory diagram for explaining how depth center point is selected.

FIGS. 15A and 15B are explanatory diagrams for explaining how the depth center point is selected. Assume that the motion pattern of the process target image is "movement toward deeper side in depth direction" or "movement toward front side in depth direction". Then, as shown in FIG. 15A, with respect to a center point candidate 143 which is a correct depth center point, the direction of each origin vector which connects the center point candidate 143 and the origin of each motion vector is close to the direction of the motion vector whose origin is a position indicated by the origin vector. For the "movement toward deeper side in depth direction", the origin vector and the motion vector are forward-directed, whereas for the "movement toward front side in depth direction", these are backward-directed. On the other hand, when the relation between each origin vector calculated with respect to a center point candidate 145 which is not the depth center point, and each of the corresponding motion vector is examined, as shown in FIG. 15B, there is no coincidence between their directions. When the origin vector and the motion vector are close to each other in terms of direction, it means that the angle formed between them is close to 0°, or 180°, whereby the absolute value of the inner product of the origin vector and the motion vector (motion-vector inner product) is close to "1". Thus, the average of the motion-vector inner products is calculated for each center point candidate, and the center point candidate for which the absolute value of the average of motion-vector inner products is maximum is selected as the depth center point. Here, if the motion vector is calculated at a position extremely close to the depth center point, the motion vector sometimes becomes 0 vector. For the 0 vector, when the average of the motion-vector inner product is positive, the motion-vector inner product is set to be "1.0", whereas when the average is negative, the motion-vector inner product is set to "−1.0".

Subsequently, the image-motion-pattern classifying unit 752 calculates the sum of the number of matching failures and the number of motion vectors for which the absolute value of motion-vector inner product from the depth center point is equal to or smaller than the previously set reference inner product, in other words, the number of motion vectors whose direction does not coincide with the direction of origin vector (corresponding to the depth direction), as shown in FIG. 13. Then, when the calculated number is smaller than a predetermined number previously set as a threshold for determination in step S79 (No in step S79), the image-motion-pattern classifying unit 752 proceeds to step S81. When the calculated number is equal to or larger than the predetermined number (Yes in step S79), the process ends. This is because, when the number of matching failures is large, or when there are many motion vectors whose direction does not coincide with the direction of the origin vector, the result of the depth-direction movement determination can be considered not to be reliable, and therefore, the process of step S81 and subsequent steps in the depth-direction movement determination is not performed. Specifically, when the average of motion-vector inner product is positive, a motion vector for which the motion-vector inner product is equal to or smaller than a predetermined lower limit inner product is determined to be a vector whose direction does not coincide with the direction of origin vector. When the average of motion-vector inner product is negative, a motion vector for which the motion-vector inner product is equal to or larger than a predetermined upper limit inner product is determined to be a vector whose direction does not coincide with the direction of origin vector. Then, it is determined whether the sum of the number of motion vectors whose direction does not coincide with the direction of origin vector and the number of matching failures is equal to or larger than a predetermined number.

Figure 16:
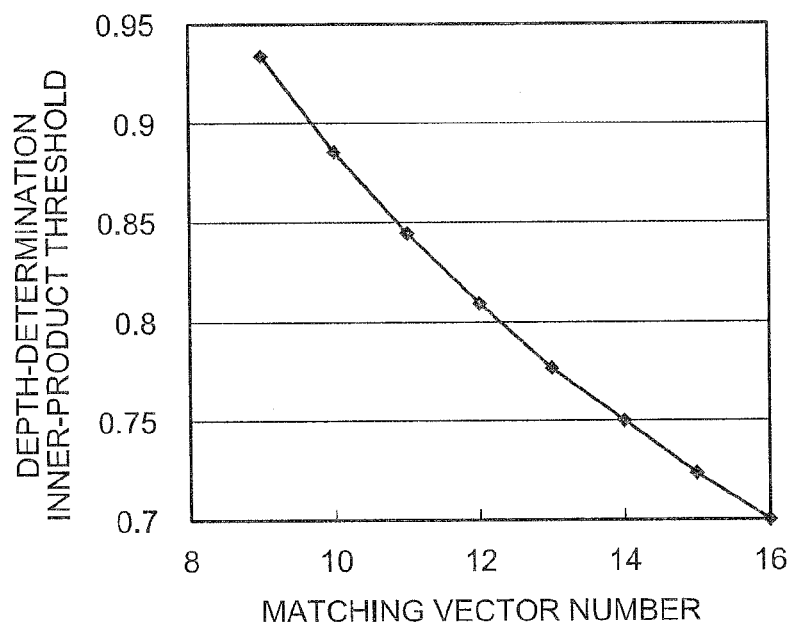
FIG. 16 is a graph of an example of depth-determination inner-product threshold.

In step S81, the image-motion-pattern classifying unit 752 sets a depth-determination inner-product threshold and a front-determination inner-product threshold based on the matching vector number. FIG. 16 is a graph for explaining how the depth-determination inner-product threshold is set, where a horizontal axis represents the matching vector number while a vertical axis represents the depth-determination inner-product threshold, and an example of depth-determination inner-product threshold set corresponding to the matching vector number is shown. As shown in FIG. 16, the depth-determination inner-product threshold is set so that the value thereof approaches "1" as the matching vector number decreases. This is because when the number of motion vectors employed for the depth-direction movement determination is small, it becomes more likely that the image motion pattern of the process target image accidentally falls into the category of "movement toward deeper side in depth direction". Therefore the depth-determination inner-product threshold is set high.

In practice, the depth-determination inner-product threshold is calculated according to following equation (3) based on a reference depth-determination inner-product threshold previously set. Here, $V_b'$ represents the depth-determination inner-product threshold, $V_b$ represents the reference depth-determination inner-product threshold, p represents the number of motion vectors for which the matching is successful, N represents the number of motion vectors when all matching is successful, and $\alpha_b$ represents conversion coefficient.

$$V_b' = V_b \times \left(\frac{N}{p}\right)^{\alpha_b} \quad (3)$$

Figure 17:
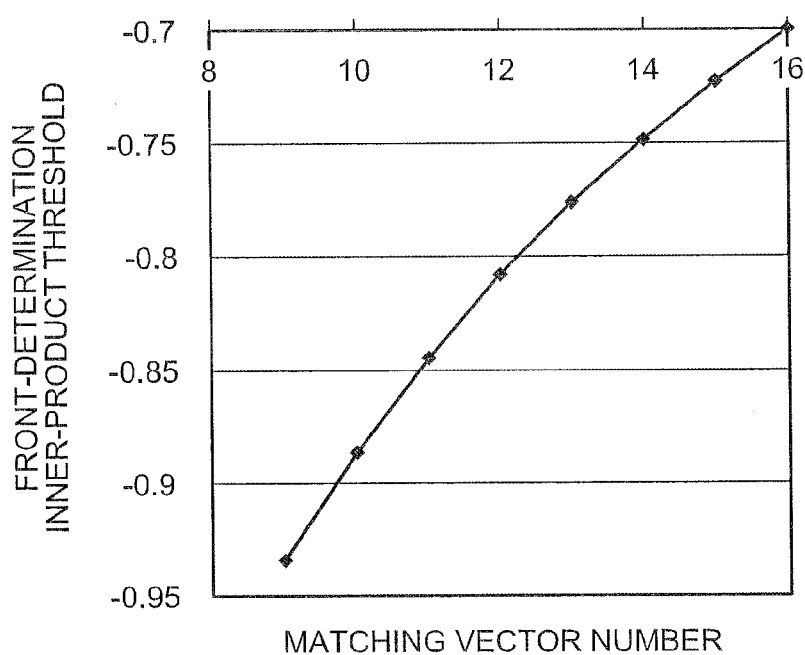
FIG. 17 is a graph of an example of front-determination inner-product threshold.

FIG. 17 is a graph for explaining how the front-determination inner-product threshold is set, where a horizontal axis represents the matching vector number while a vertical axis represents the front-determination inner-product threshold, and an example of front-determination inner-product threshold set corresponding to the matching vector number is shown. As shown in FIG. 17, the front-determination inner-product threshold is set so that the value thereof approaches "−1" as the matching vector number decreases. This is because when the number of motion vectors employed for the depth-direction movement determination is small, it becomes more likely that the image motion pattern of the process target image accidentally falls into the category of "movement toward front side in depth direction". Therefore the front-determination inner-product threshold is set low.

In practice, the front-determination inner-product threshold is calculated according to following equation (4) based on a reference front-determination inner-product threshold previously set. Here, $V_d'$ represents the front-determination inner-product threshold, $V_d$ represents the reference front-determination inner-product threshold, p represents the number of motion vectors for which the matching is successful, N represents the number of motion vectors when all matching is successful, and $\alpha_d$ represents conversion coefficient.

$$V_d' = V_d \times \left(\frac{N}{p}\right)^{\alpha_d} \quad (4)$$

Figure 18A:
FIG. 18A is a view of an example of the former time-series image.
Figure 18B:
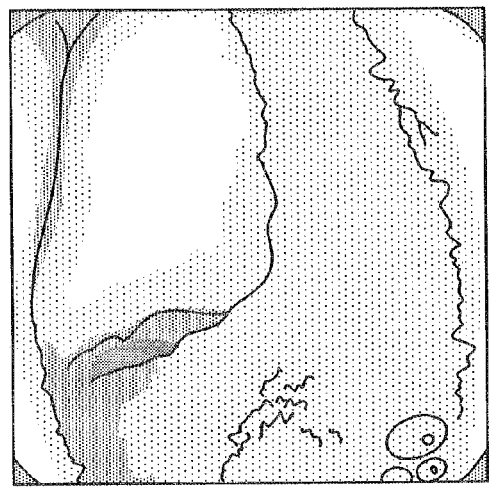
FIG. 18B is a view of an example of the process target image.
Figure 18C:
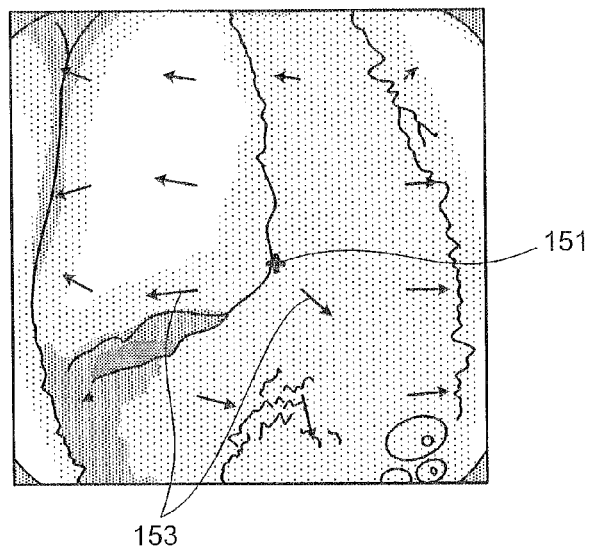
FIG. 18C is a view in which motion vectors calculated based on the former time-series image of FIG. 18A and the process target image of FIG. 18B are shown in the process target image.

Then, the image-motion-pattern classifying unit 752 determines on the average of motion-vector inner products calculated for the depth center in step S75 as shown in FIG. 13. The image-motion-pattern classifying unit 752 classifies, when the average of motion-vector inner products is equal to or larger than the depth-determination inner-product threshold set in step S81 (Yes in step S83), the image motion pattern of the process target image as "movement toward deeper side in depth direction" (step S85). In the embodiment, the image motion pattern of the process target image is classified as "movement toward deeper side in depth direction" when the average of motion-vector inner products calculated for the depth center in step S75 is equal to or larger than the depth-determination inner-product threshold set in step S81, though the manner of classification is not limited thereto. For example, such configuration is possible in which the image motion pattern of the process target image is classified as "movement toward deeper side in depth direction" when at least one of values including the average value, minimum value, and fluctuation of the motion-vector inner product is within a range of threshold set for the determination of "movement toward deeper side in depth direction". FIG. 18A is a view of an example of the former time-series image, FIG. 18B is a view of an example of the process target image, and FIG. 18C is a view of motion vectors in the process target image calculated based on the former time-series image of FIG. 18A and the process target image of FIG. 18B. Further, in FIG. 18C, a depth center point 151 is shown. As shown in FIG. 18C, when each of motion vectors 153 is directed in substantially the same direction with a corresponding origin vector (direction from the depth center point 151 to the motion vector), the image motion pattern is classified as "movement toward deeper side in depth direction".

Figure 19A:
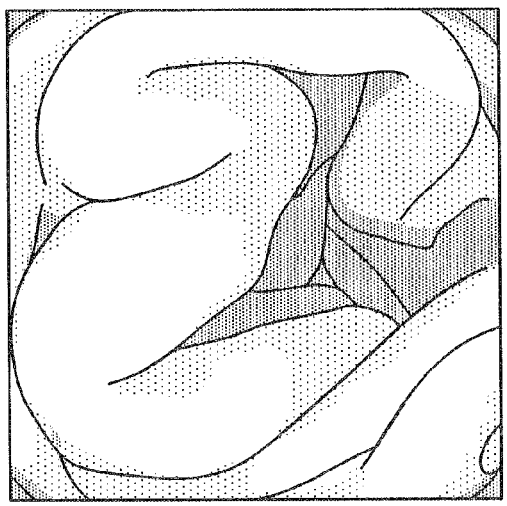
FIG. 19A is a view of an example of the former time-series image.
Figure 19B:
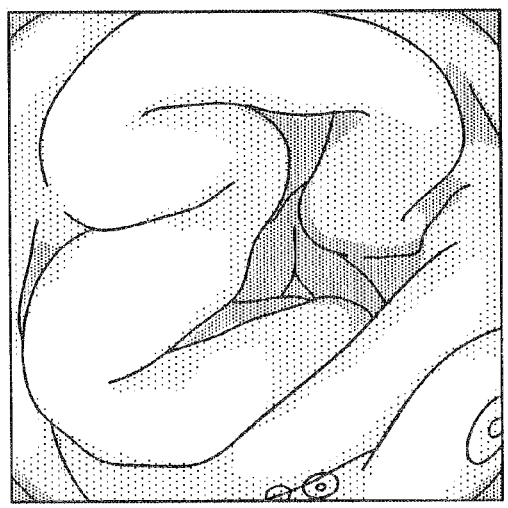
FIG. 19B is a view of an example of the process target image.
Figure 19C:
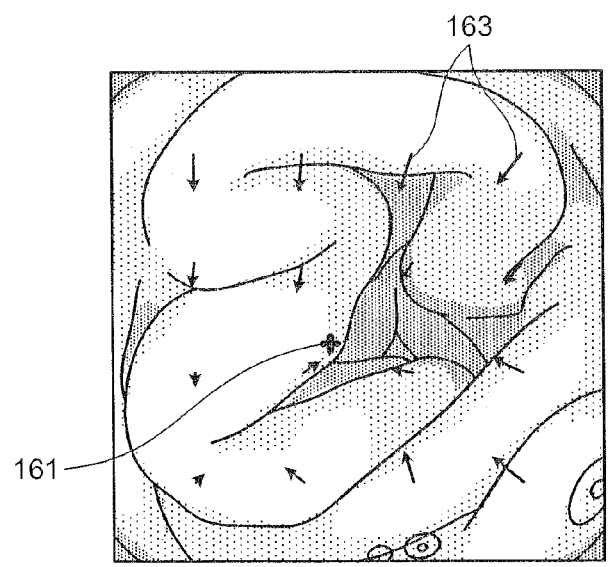
FIG. 19C is a view in which motion vectors calculated based on the former time-series image of FIG. 19A and the process target image of FIG. 19B are shown in the process target image.

Further, the image-motion-pattern classifying unit 752 determines on the average of motion-vector inner products calculated for the depth center in step S75 as shown in FIG. 13. The image-motion-pattern classifying unit 752 classifies, when the average of motion-vector inner products is equal to or smaller than the front-determination inner-product threshold set in step S81 (Yes in step S87), the image motion pattern of the process target image as "movement toward front side in depth direction" (step S89). In the embodiment, the image motion pattern of the process target image is classified as "movement toward front side in depth direction" when the average of motion-vector inner products calculated for the depth center in step S75 is equal to or smaller than the front-determination inner-product threshold set in step S81, though the manner of classification is not limited thereto. For example, such configuration is possible in which the image motion pattern of the process target image is classified as "movement toward front side in depth direction" when at least one of values including the average value, maximum value, and fluctuation of the motion-vector inner product is within a range of threshold set for the determination of "movement toward front side in depth direction". FIG. 19A is a view of an example of the former time-series image, FIG. 19B is a view of an example of the process target image, and FIG. 19C is a view of motion vectors in the process target image calculated based on the former time-series image of FIG. 19A and the process target image of FIG. 19B. Further, in FIG. 19C, a depth center point 161 is shown. When each of motion vectors 163 is directed substantially in an opposite direction from the corresponding origin vector (direction from the depth center point 161 to the motion vector) as shown in FIG. 19C, the image motion pattern is classified as "movement toward front side in depth direction".

Here, the image motion pattern is classified as "movement toward deeper side in depth direction" when the average of motion-vector inner products is equal to or larger than the depth-determination inner-product threshold, though the image motion pattern can be classified based on an angle formed by the motion vector and the origin vector. For example, the movement is determined to be toward the depth direction when the calculated average of angle formed by each of the motion vectors and the origin vector is equal to or smaller than a predetermined value previously set as a threshold. When the motion vector and the origin vector are substantially in the same direction with each other, the image motion pattern may be classified as "movement toward deeper side in depth direction", while the image motion pattern is classified as "movement toward front side in depth direction" when the motion vector and the origin vector are substantially in opposite directions from each other. Then, the image-motion-pattern classifying unit 752 returns to step S21 of FIG. 5 and proceeds to step S23.

In step S23, the image-motion-pattern classifying unit 752 determines whether the image motion pattern is "movement toward deeper side in depth direction" or not. When image motion pattern is classified as "movement toward deeper side in depth direction" as a result of the depth-direction movement determination process in step S21 (Yes in step S23), the image-motion-pattern classifying unit 752 finishes the process. On the other hand, when the image motion pattern is not "movement toward deeper side in depth direction" (No in step S23), subsequently the image-motion-pattern classifying unit 752 determines whether the image motion pattern is "movement toward front side in depth direction" or not. When the image motion pattern is classified as "movement toward front side in depth direction" as a result of the depth-direction movement determination process in step S21 (Yes in step S25), the image-motion-pattern classifying unit 752 finishes the process. When the image motion pattern is not "movement toward front side in depth direction" (No in step S25), the image-motion-pattern classifying unit 752 classifies the image motion pattern as "scene change" (step S27).

Figure 20A:
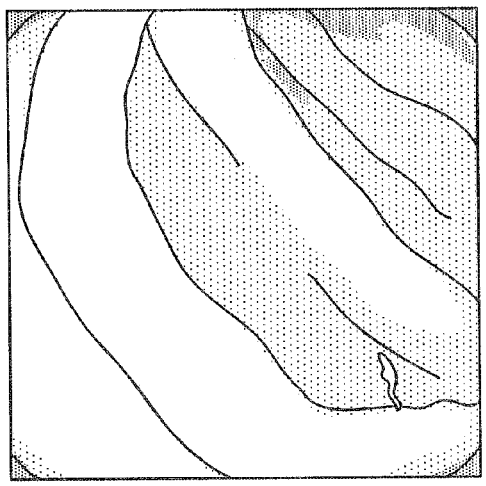
FIG. 20A is a view of an example of the former time-series image.
Figure 20B:
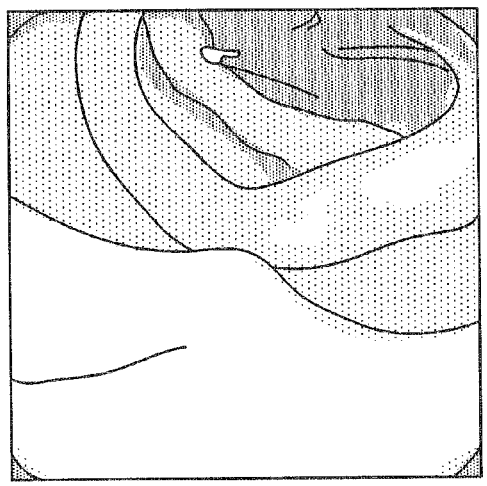
FIG. 20B is a view of an example of the process target image.
Figure 20C:
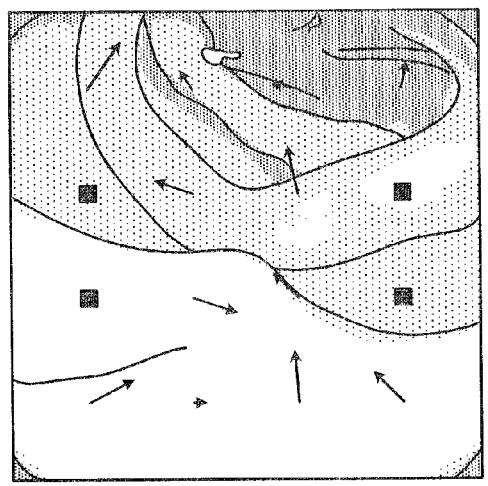
FIG. 20C is a view in which motion vectors calculated based on the former time-series image of FIG. 20A and the process target image of FIG. 20B are shown in the process target image.

In brief, the image-motion-pattern classifying unit 752 classifies the image motion pattern as "scene change" even when the number of templates for which the matching is successful is determined to be larger than the reference number of successes in step S11, if the image motion pattern is not set as any of "no-motion", "parallel movement", "movement toward deeper side in depth direction", and "movement toward front side in depth direction" in the process from step S13 to step S25. FIG. 20A is a view of an example of the former time-series image, FIG. 20B is a view of an example of the process target image, and FIG. 20C is a view of motion vectors in the process target image calculated based on the former time-series image of FIG. 20A and the process target image of FIG. 20B. When there is no regularity in the size and the direction of each motion vector in the process target image as shown in FIG. 20C and the image motion pattern cannot be determined simply as one of the no-motion, the parallel movement, or the movement in depth direction, the image motion pattern is classified as "scene change". Such can happen, for example, when the motion vector is calculated at an incorrect matching position due to lack of position where the correct template matching can be performed, or when the mucosal membrane in the body cavity actually moves irregularly when the capsule endoscope 3 picks up its image.

Then, the image-motion-pattern classifying unit 752 returns to step S2 of FIG. 3 and proceeds to step S3. The result of classification in the image-motion-pattern classification process is stored in the storage unit 740.

Next, the off-vector search process in step S3 of FIG. 3 is described. In the off-vector search process, from an intra-body image which is classified as one of "parallel movement", "movement toward deeper side in depth direction", and "movement toward front side in depth direction" among the image motion patterns, a motion vector which does not match the selected image motion pattern is searched and extracted as an off-vector. When the image includes many motion vectors which does not match the image motion pattern (i.e., off-vectors), the image motion pattern is changed to "scene change". Further, the motion vector which is set as an off-vector in the off-vector search process is not employed as a target of the newly-appearing-image-rate estimation process in a subsequent stage.

Figure 21:
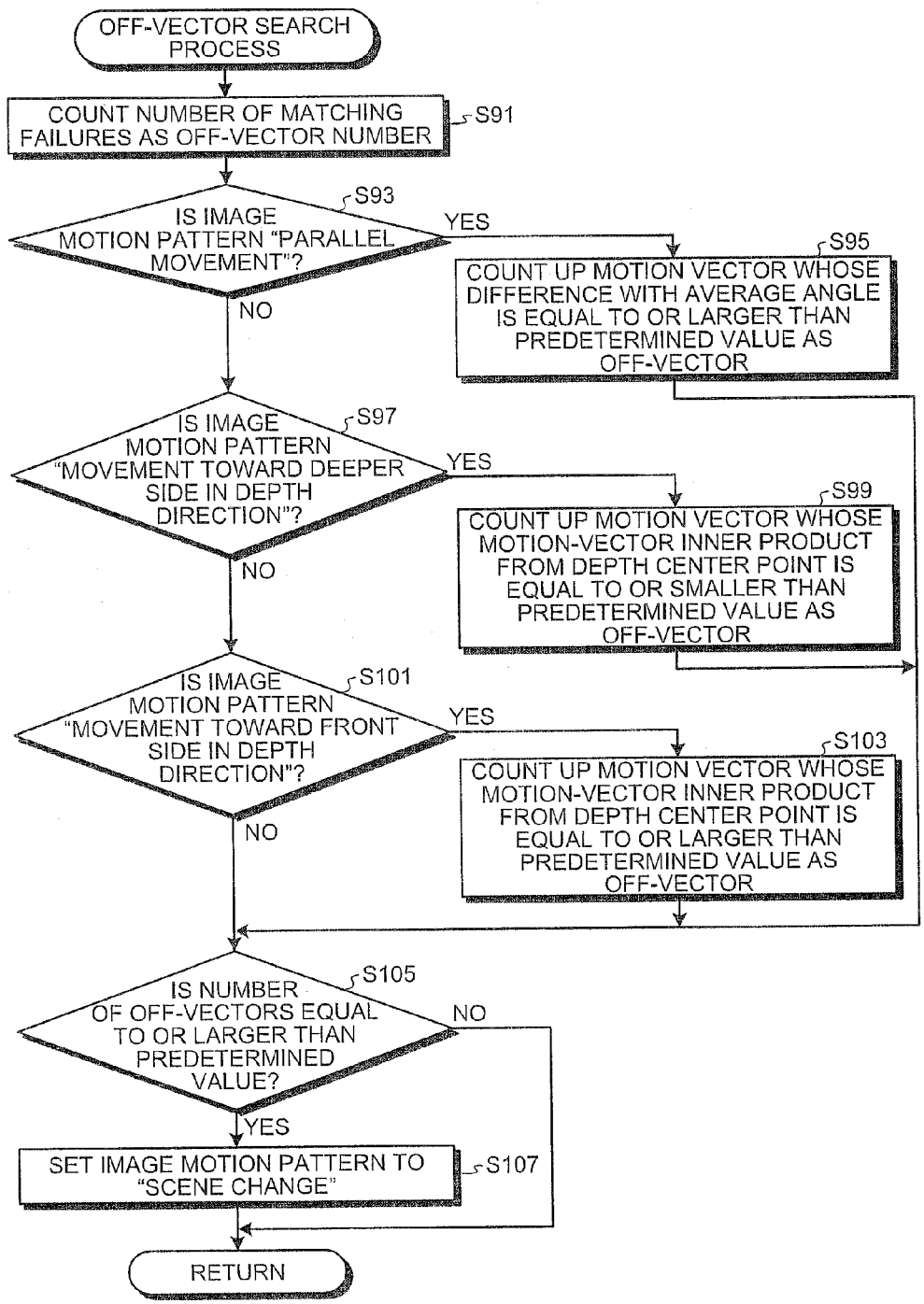
FIG. 21 is a flowchart of detailed process procedures of an off-vector search process.

FIG. 21 is a flowchart of detailed process procedures of the off-vector search process. The off-vector search unit 753 first counts the number of matching failures as an off-vector number (step S91).

Subsequently, the off-vector search unit 753 determines the image motion pattern of the process target image. When the image motion pattern is "parallel movement" (Yes in step S93), the off-vector search unit 753 calculates the difference between each motion vector in the process target image and the average angle of the motion vector in the process target image calculated in step S55 of FIG. 10. The off-vector search unit 753 updates the count of the off-vector number by treating the motion vector as an off-vector when the calculated difference is equal to or larger than a predetermined value previously set as a threshold for determination in step S95 (step S95).

When the image motion pattern of the process target image is "movement toward deeper side in depth direction" (Yes in step S97), the off-vector search unit 753 updates the count of off-vector number by treating the motion vector as an off-vector when the motion-vector inner product calculated in step S73 of FIG. 13 is equal to or smaller than a predetermined value previously set as a threshold for determination in step S99 (step S99).

When the image motion pattern of the process target image is "movement toward front side in depth direction" (Yes in step S101), the off-vector search unit 753 determines on the motion-vector inner product calculated in step S73 of FIG. 13. The off-vector search unit 753 updates the count of the off-vector number by treating the motion vector as an off-vector when the motion-vector inner product is equal to or larger than a predetermined value previously set as a threshold for determination in step S103 (step S103).

Then, the off-vector search unit 753 determines the counted off-vector number. When the counted off-vector number is equal to or larger than a predetermined value previously set as a threshold for determination in step S105 (Yes in step S105), the off-vector search unit 753 changes the image motion pattern of the process target image to "scene change" (step S107). Then, the off-vector search unit 753 returns to step S3 of FIG. 3 and proceeds to step S4.

Next, the newly-appearing-image-rate estimation process in step S4 of FIG. 3 is described. In the newly-appearing-image-rate estimation process, a newly-appearing rate, i.e., a rate of a region which is newly generated in the process target image after the former time-series image is calculated according to the image motion pattern determined as a result of classification. For example, a possible range of the newly-appearing rate is set from "0.0" to "1.0", and the value of the newly-appearing rate is estimated to approach "1.0" as the change from the former time-series image becomes larger. If there is no change in images, the newly-appearing rate is estimated to be "0.0".

Figure 22:
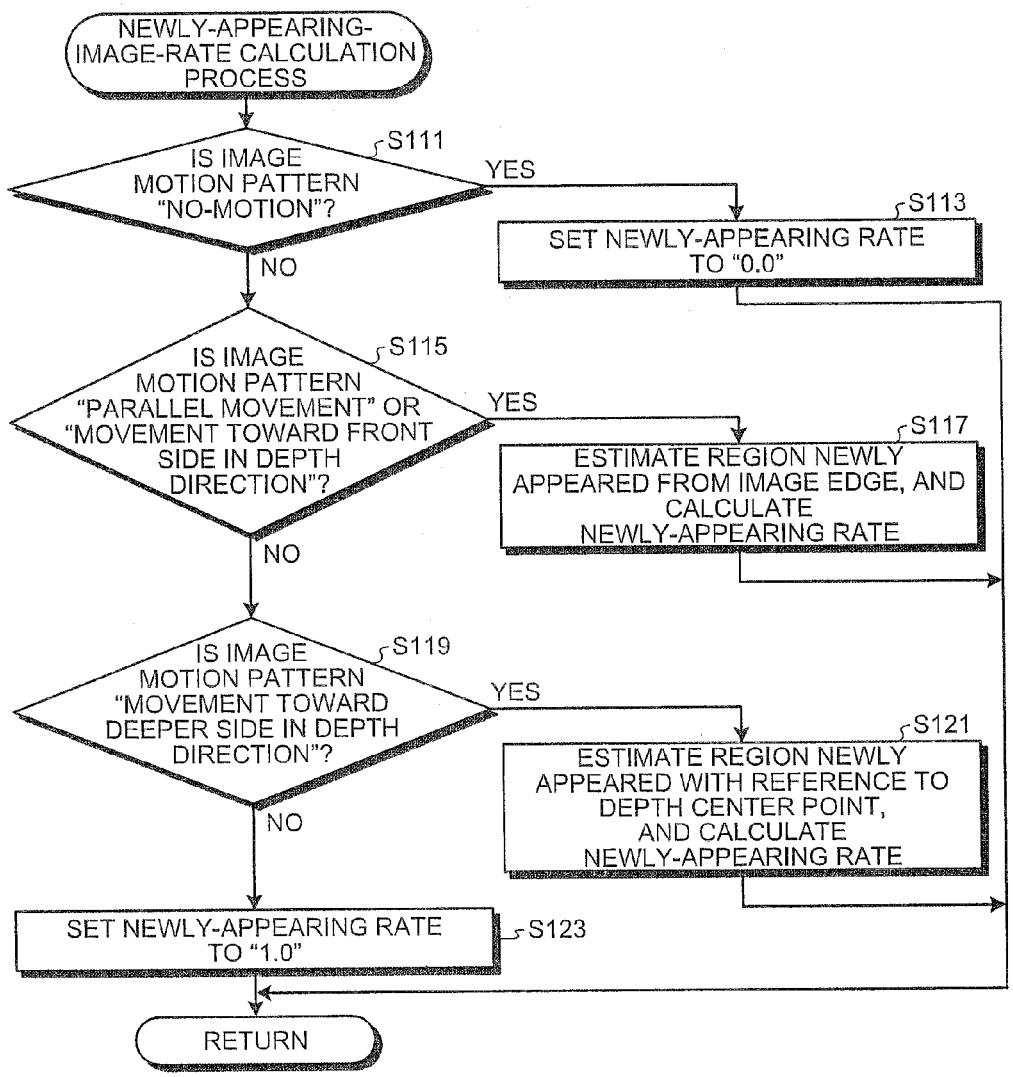
FIG. 22 is a flowchart of detailed process procedures of a newly-appearing-image-rate estimation process.

FIG. 22 is a flowchart of detailed process procedures of the newly-appearing-image-rate estimation process. Firstly, the newly-appearing-image-rate estimating unit 754 determines the image motion pattern of the process target image. When the image motion pattern is "no-motion" (Yes in step S111), the image can be considered to have undergone insignificant changes, and therefore, the newly-appearing rate is set to "0.0" (step S113).

When the image motion pattern is one of "parallel movement" and "movement toward front side in depth direction" (Yes in step S115), the newly-appearing-image-rate estimating unit 754 performs estimation of the newly-appeared region appeared from the edge of the image and calculates the newly-appearing rate (step S117).

Figure 23A:
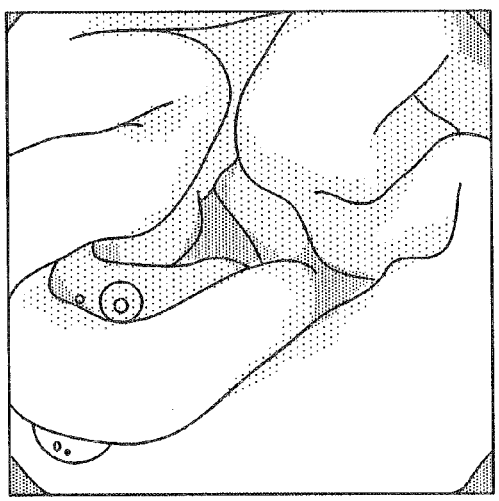
FIG. 23A is a view of an example of the former time-series image.
Figure 23B:
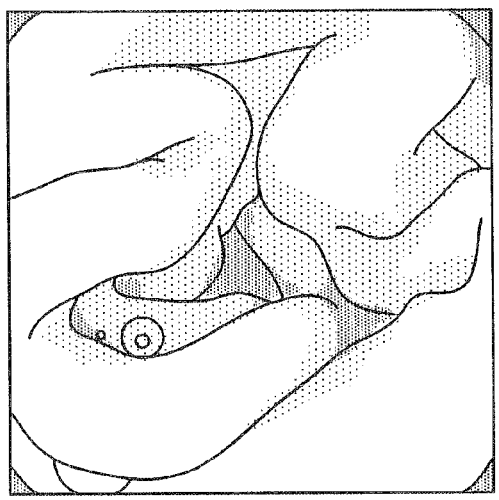
FIG. 23B is a view of an example of the process target image, for which a motion pattern found between the former time-series image of FIG. 23A is classified as "parallel movement"
Figure 23C:
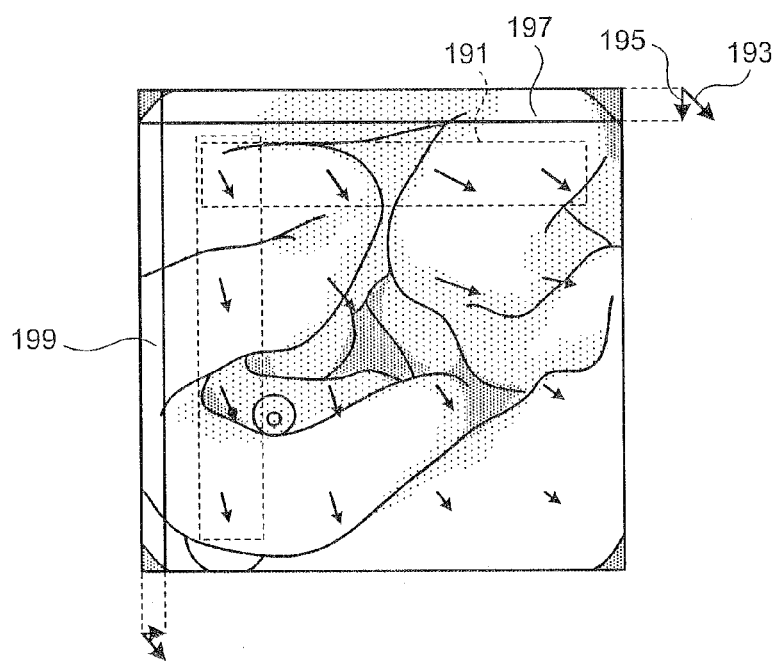
FIG. 23C is a view of a newly-appeared region estimated in the process target image of FIG. 23B.

FIG. 23A is a view of an example of the former time-series image. FIG. 23B is a view of an example of the process target image, for which an image motion pattern found between the former time-series image of FIG. 23A is classified as "parallel movement". FIG. 23C is a view of a newly-appeared region estimated in the process target image of FIG. 23B. When the image motion pattern is "parallel movement", a new region which does not appear in the former time-series image is expected to appear in the process target image from the edge of the image corresponding to the motion vector. Hence, the newly-appearing-image-rate estimating unit 754 estimates the newly-appeared region using a motion vector of a line closest to the image edge with respect to each image edge. Specifically, the newly-appearing-image-rate estimating unit 754 finds the average of motion vector (motion vector average) in the line closest to each image edge, and estimates the newly-appeared region at each image edge based on a projection component in a direction orthogonal to each image edge. For example, when an upper edge of the process target image is focused, a motion vector in an uppermost row 191 is employed as shown in FIG. 23C, and a motion vector average 193 is found as shown outside a frame. Then, a region 197 which has the width of a projection component 195 in the direction orthogonal to the upper edge of the image (up-down direction of FIG. 23) is estimated as a newly-appeared region at the upper edge of the image. Similarly, a newly-appeared region is estimated for each image edge. The rate of the sum of eventually obtained regions 197 and 199 to the entire image is set as a newly-appearing rate. Among the motion vectors on the lines closest to the image edges, those vectors which are counted as off-vectors in the off-vector search process (FIG. 21) are not set as the process target. Further, when all the matching fails and no motion vector is obtained, or when all obtained vectors are off-vectors on the lines closest to the image edges, motion vectors on inner lines are employed for the estimation of the newly-appearing regions at the target image edges.

Figure 24A:
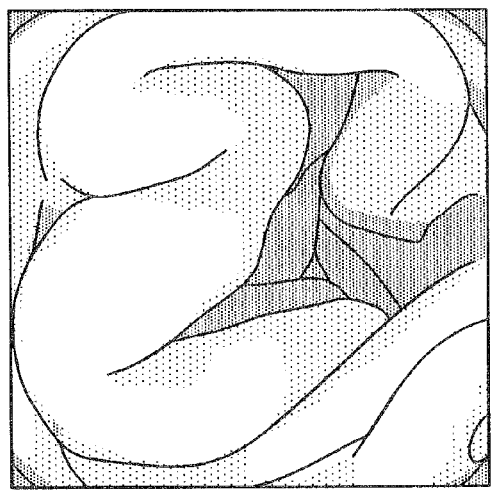
FIG. 24A is a view of an example of the former time-series image.
Figure 24B:
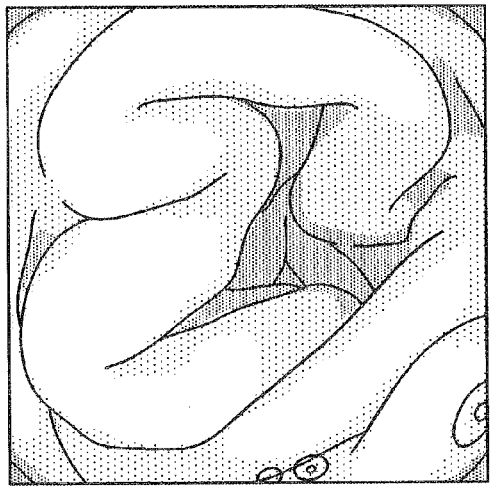
FIG. 24B is a view of an example of the process target image, for which a motion pattern found between the former time-series image of FIG. 24A is classified as "movement toward front side in depth direction"
Figure 24C:
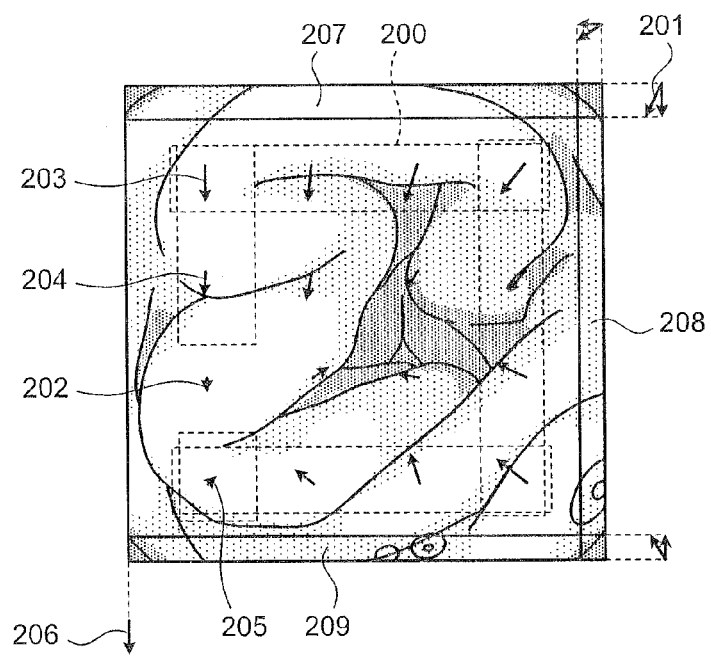
FIG. 24C is a view of a newly-appeared region estimated in the process target image of FIG. 24B.

FIG. 24A is a view of an example of the former time-series image. FIG. 24B is a view of an example of the process target image, for which an image motion pattern found between the former time-series image of FIG. 24A is classified as "movement toward front side in depth direction". FIG. 24C is a view of a newly-appeared region estimated in the process target image of FIG. 24B. When the image motion pattern is "movement toward front side in depth direction", a new region which does not appear in the former time-series image is expected to appear in the process target image from the edge of the image corresponding to the motion vector. Hence, the newly-appearing-image-rate estimating unit 754 estimates the newly-appeared region using the motion vectors on the line closest to the image edge for each image edge similarly to the case of "parallel movement". For example, if an upper edge of the process target image is focused, motion vectors in an uppermost row 200 is employed as shown in FIG. 24C, and a motion vector average 201 is found as shown outside a frame. Further, at the left edge of the process target image, a motion vector average 206 is found based on motion vectors 203, 204, and 205 other than a motion vector 202 which is counted as the off-vector among the motion vectors in the leftmost column. The rate of the sum of eventually obtained regions 207, 208, and 209 to the entire image is set as a newly-appearing rate.

When the image motion pattern is "movement toward deeper side in depth direction" (Yes in step S119), the newly-appearing-image-rate estimating unit 754 estimates the newly-appeared region with reference to the depth center point and calculates the newly-appearing rate (step S121).

Figure 25A:
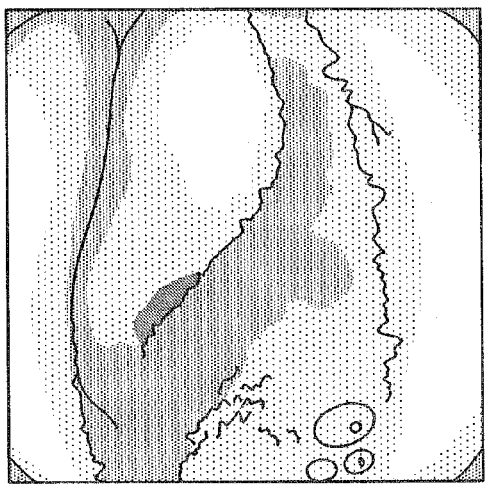
FIG. 25A is a view of an example of the former time-series image.
Figure 25B:
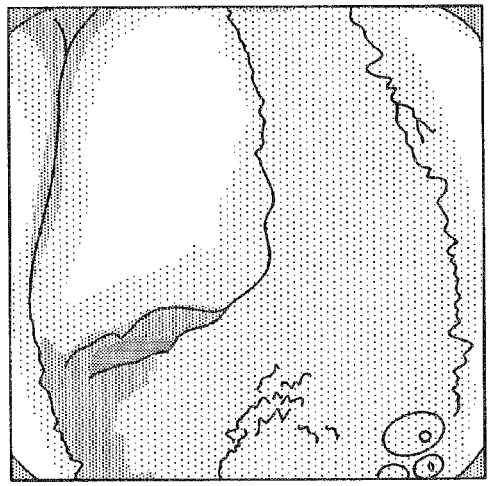
FIG. 25B is a view of an example of the process target image, for which a motion pattern found between the former time-series image of FIG. 25A is classified as "movement toward deeper side in depth direction"
Figure 25C:
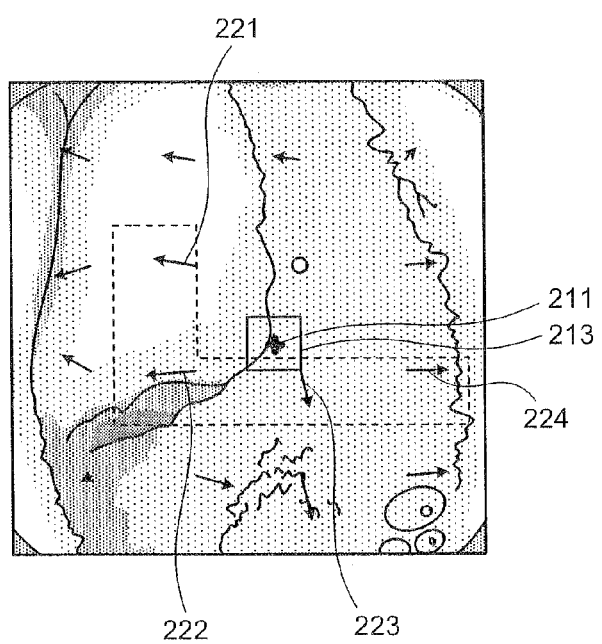
FIG. 25C is a view of a newly-appeared region estimated in the process target image of FIG. 25B.
Figure 26:
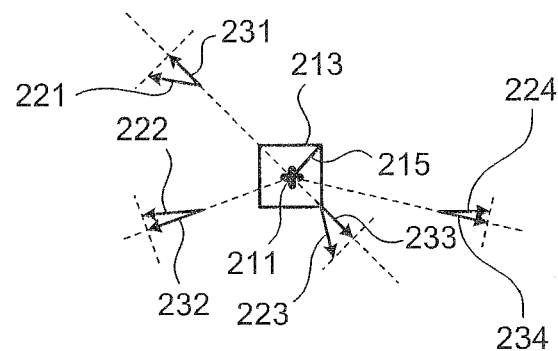
FIG. 26 is an explanatory diagram for explaining how the newly-appeared region is estimated when the image motion pattern is "movement toward deeper side in depth direction"

FIG. 25A is a view of an example of the former time-series image. FIG. 25B is a view of an example of the process target image, for which an image motion pattern found between the former time-series image of FIG. 25A is classified as "movement toward deeper side in depth direction". FIG. 25C is a view of a newly-appeared region estimated in the process target image of FIG. 25B. When the image motion pattern is "movement toward deeper side in depth direction", a new region which does not appear in the former time-series image is expected to appear in the process target image from the depth center point. Hence, the newly-appearing-image-rate estimating unit 754 estimates the newly-appeared region using a predetermined number of motion vectors calculated at template positions near the depth center point. Specifically, the newly-appearing-image-rate estimating unit 754 selects the predetermined number of motion vectors starting from the one whose distance from the depth center point is shorter. Subsequently, the newly-appearing-image-rate estimating unit 754 calculates the length of each projection component in a linear direction connecting the depth center point and the origin of each motion vector, and obtains the average thereof (projection component average). The newly-appearing-image-rate estimating unit 754 then estimates a rectangular region which has twice the length of the obtained projection component average as its diagonal line with reference to the depth center point as a newly-appeared region. For example, the newly-appeared region is estimated based on four vectors 221 to 224 calculated near the depth center point 211 in FIG. 25C. FIG. 26 is an explanatory diagram for explaining how the newly-appeared region is estimated when the image motion pattern is "movement toward deeper side in depth direction", where the depth center point 211 of FIG. 25C and four vectors 221 to 224 nearby are extracted. As shown in FIG. 26, projection components 231 to 234 are found for the motion vectors 221 to 224, respectively, in the linear direction connecting the depth center point 211 and the origin of the motion vector, and the projection component average is obtained. The newly-appearing-image-rate estimating unit 754 then estimates a rectangular region 213 which has twice the length 215 of the obtained projection component average as its diagonal line with reference to the depth center point 211 as a newly-appeared region.

When the image motion pattern is "scene change", the entire process target image shows a different portion from the portion appears in the former time-series image and it can be considered that the entire image has been changed. In this case, the newly-appearing-image-rate estimating unit 754 sets the newly-appearing rate to "1.0" (step S123).

Next, the display-time determination coefficient calculation process in step S5 of FIG. 3 is described. The display-time determination coefficient calculating unit 755 converts the newly-appearing rate obtained as a result of the newly-appearing-image-rate estimation process into a display-time determination coefficient T using a conversion curve represented by following equation (5).

$$T = \alpha \times S^{\gamma} \tag{5}$$

Figure 27:
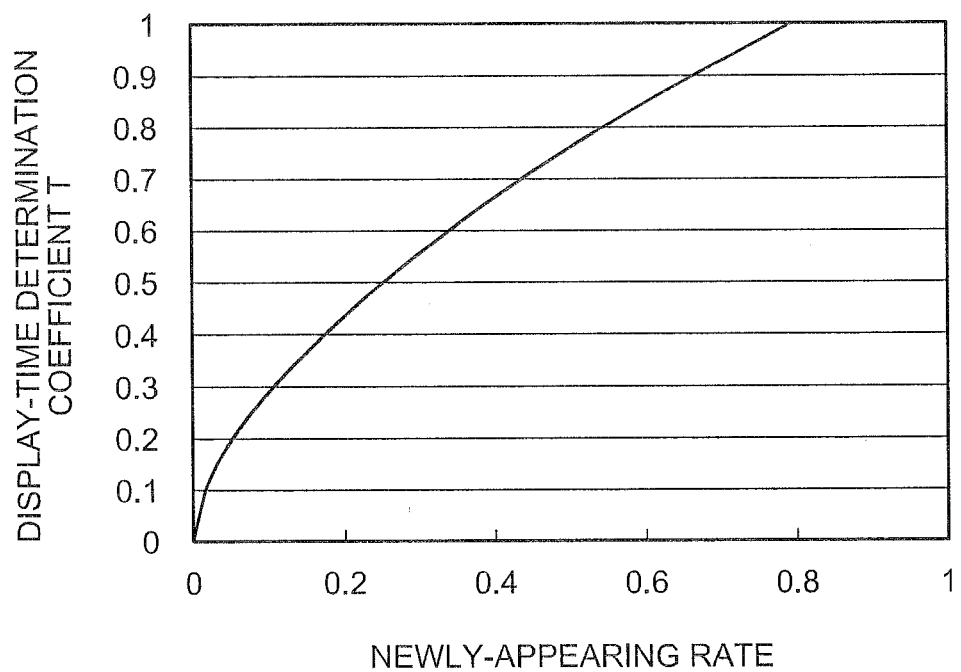
FIG. 27 is a graph of an example of conversion curve for converting a newly-appearing rate into a display-time determination coefficient.

When T>1.0, T is set as T=1.0. Here, S represents newly-appearing rate, α represents display-time calculation coefficient, and γ represents display-time calculation power coefficient. FIG. 27 is a graph of conversion curve represented by the equation (5). It is expected that once the newly-appearing rate S exceeds a predetermined level, an observer finds it difficult to find correspondence between images and feels that the image is substantially a new image. Hence, in the embodiment, a degree at which the observer feels as described above is determined empirically as α in the equation (5). Further, as the range of the value of newly-appearing rate calculated with respect to each motion pattern except for the no-motion and the scene change differs depending on a search range at the time of motion-vector calculation, the range of the value of display-time determination coefficient may be made adjustable according thereto. Hence, in the embodiment, the degree of adjustment is empirically determined as γ in the equation (5).

Further, for example, when the interior of a lumen in the body is imaged, among objects of imaging (subjects) at the time of imaging, an object which is present relatively close to the position of the capsule endoscope 3 and appears near the image edge may appears in a different size in the image from an object which is far from the capsule endoscope 3 and appears near the depth center point of the image. Further, an observer may feel that the image changes in a manner not proportional to the size of the calculated newly-appeared region when the newly-appeared region starts to appear from the image edge and when the newly-appeared region starts to appear from a portion around the depth center point. Hence, when the image motion pattern is "movement toward deeper side in depth direction", a previously obtained newly-appearing rate is multiplied by a predetermined coefficient before the calculation of the display-time determination coefficient T.

The display-time determination coefficient T takes a value within the range from "0.0" to "1.0", and takes a value of "0.0" when the image contents does not change substantially from the former time-series image, and the display time becomes shortest. On the other hand, when the image contents change significantly from the former time-series image, the display-time determination coefficient T takes the value of "1.0", and the image display time becomes longest. In other words, the found display-time determination coefficient T is employed as a variable of the display time Time of the intra-body image calculated by following equation (6), for example. In the equation (6), MaxTime represents the longest display time of one intra-body image, and MinTime represents the shortest display time of one intra-body image. The value of each of the longest display time and the shortest display time may be previously set, or configured to be settable and changeable by a user operation or the like.

$$\text{Time} = (\text{MaxTime} - \text{MinTime}) \times T + \text{MinTime} \tag{6}$$

As described above, in the embodiment, the intra-body images which are time-series images are classified into the image motion patterns which represent how the image as a whole moves, based on the motion vectors calculated relative to another intra-body image which precedes in time series. Then, the newly-appearing rate of the region which appears anew after the former time-series image is calculated with the use of the motion vector corresponding to the image motion pattern, and the display-time determination coefficient is calculated based on the newly-appearing rate of the image. Thus, the display time of each of the intra-body images can be adjusted according to the change in the appearance of the image as observed by the observer with the use of the motion vector, whereby each intra-body image can be displayed for an appropriate display time. Therefore, an image, in which a site which does not appear in previous images occupies a large area, would not be skipped or displayed only for a short time. Thus, the observer would not fail to notice the display contents, and further, as an image in which an already-observed site occupies a large area is displayed only for a short time period, the observation efficiency can be enhanced, and the observer can efficiently grasp the contents of intra-body images.

In the embodiment described above, the image is classified as one of the image motion patterns including "no-motion", "parallel movement", "movement toward deeper side in depth direction", "movement toward front side in depth direction", and "scene change". And the configuration is described as performing the newly-appearing-image-rate calculation by a manner corresponding to the classification of the image motion pattern, though the present invention is not limited by the embodiment. For example, it is possible to set at least one of the image motion patterns including "no-motion", "parallel movement", "movement toward deeper side in depth direction", "movement toward front side in depth direction", and "scene change" as a target of determination, and to make such a configuration that the newly-appearing rate is calculated in a manner corresponding to the classification of the image motion pattern set as the determination target.

Further, in the embodiment above, the display of time-series intra-body images picked up by the capsule endoscope 3 is described, though the present invention is not limited thereto. The present invention is similarly applicable to a case where time-series images are sequentially displayed, for example, and an image with a high newly-appearing rate may be displayed for a long time, while an image with a low newly-appearing rate may be displayed for a short time, among images constituting the time-series images.

According to the embodiment, the display time of the image can be set according to the newly-appearing rate which is a rate of a newly-appeared region in an image. Hence, the observer is prevented from overlooking the display contents, and at the same time, contents of plural images constituting the time-series images can be efficiently grasped.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus which processes time-series images picked up by an imaging device in time series, comprising:
a motion-vector calculating unit that calculates a motion vector between plural images constituting the time-series images with respect to plural pixel regions set in the image;
a newly-appearing-rate estimating unit that estimates a newly-appearing rate, which is a rate of a newly-appeared region in an image between the plural images, based on a motion vector calculated by the motion-vector calculating unit; and
a display-time calculating unit that calculates a display time of the image according to a newly-appearing rate estimated by the newly-appearing-rate estimating unit.

2. The image processing apparatus according to claim 1, wherein
the newly-appearing-rate estimating unit includes an image-edge newly-appearing-region estimating unit that estimates a region which newly appears at an image edge.

3. The image processing apparatus according to claim 2, wherein
the image-edge newly-appearing-region estimating unit estimates a region which newly appears using a motion vector calculated in a pixel region near the image edge.

4. The image processing apparatus according to claim 1, wherein
the newly-appearing-rate estimating unit includes an advancing-direction newly-appearing-region estimating unit that estimates a region which newly appears with reference to a point which indicates a destination of the imaging device in the image, between the plural images.

5. The image processing apparatus according to claim 4, wherein
the advancing-direction newly-appearing-region estimating unit estimates a newly-appearing region using a motion vector calculated in a pixel region near the advancing-direction position.

6. The image processing apparatus according to claim 1 wherein
the newly-appearing-rate estimating unit includes a motion-pattern classifying unit that classifies a motion pattern of an image based on a motion vector calculated by the motion-vector calculating unit as at least one of motion patterns, and the newly-appearing-rate estimating unit estimates the newly-appearing rate based on the motion pattern selected as a result of classification.

7. The image processing apparatus according to claim 6, wherein
the motion-pattern classifying unit classifies the motion pattern of the image into one of motion patterns including at least no-motion, parallel movement, movement toward deeper side in depth direction, movement toward front side in depth direction, and scene change.

8. The image processing apparatus according to claim 7, wherein
the newly-appearing-rate estimating unit estimates a region which newly appears from an image edge when the motion pattern of an image is classified as the parallel movement by the motion-pattern classifying unit.

9. The image processing apparatus according to claim 7, wherein the newly-appearing-rate estimating unit estimates a region which newly appears with reference to the advancing-direction position when the motion pattern of an image is classified as the movement toward deeper side in depth direction by the motion-pattern classifying unit.

10. The image processing apparatus according to claim 7, wherein the newly-appearing-rate estimating unit estimates a region which newly appears from an image edge when the motion pattern of an image is classified as the movement toward front side in depth direction by the motion-pattern classifying unit.

11. The image processing apparatus according to claim 7, wherein the newly-appearing-rate estimating unit estimates the newly-appearing rate to be a possible minimum value when the motion pattern of an image is classified as the no-motion by the motion-pattern classifying unit.

12. The image processing apparatus according to claim 7, wherein the newly-appearing-rate estimating unit estimates the newly-appearing rate to be a possible maximum value when the motion pattern of an image is classified as the scene change by the motion-pattern classifying unit.

13. The image processing apparatus according to claim 7, wherein
the newly-appearing-rate estimating unit estimates the newly-appearing rate to be within a range larger than a possible minimum value and smaller than a possible maximum value when the motion pattern of an image is classified as the image motion pattern other than the no-motion and the scene change by the motion-pattern classifying unit.

14. The image processing apparatus according to claim 7, wherein
the motion-pattern classifying unit classifies the motion pattern of an image to the no-motion based on a size of a motion vector in the image in the plural pixel regions.

15. The image processing apparatus according to claim 7, wherein
the motion-pattern classifying unit classifies the motion pattern of an image as the parallel movement when fluctuation of an angle of a motion vector of the image in the plural pixel regions is equal to or smaller than a predetermined threshold.

16. The image processing apparatus according to claim 7, wherein the motion-pattern classifying unit includes an advancing-direction-position search unit that searches for the advancing-direction position.

17. The image processing apparatus according to claim 7 wherein the motion-pattern classifying unit calculates an origin vector which connects the advancing-direction position and an origin of the motion vector, and classifies the motion pattern of an image as the movement toward deeper side in depth direction or the movement toward front side in depth direction based on an angle formed by the motion vector and the origin vector or an inner product of the motion vector and the origin vector.

18. The image processing apparatus according to claim 7, wherein the motion-pattern classifying unit classifies the motion pattern of an image as the scene change when a confidence value of the motion vector calculated by the motion-vector calculating unit is equal to or smaller than a predetermined threshold, or when the motion pattern of the image is not classified as any of the no-motion, parallel movement, movement toward deeper side in depth direction, and movement toward front side in depth direction.

19. The image processing apparatus according to claim 6, wherein the motion-pattern classifying unit includes an off-vector excluding unit that excludes a motion vector which has an off-value among the motion vectors in the plural pixel regions of the image, and classifies the motion pattern of the image using the motion vector other than the motion vector excluded by the off-vector excluding unit.

20. The image processing apparatus according to claim 6, wherein the newly-appearing-rate estimating unit includes an off-pattern-vector extracting unit that extracts a motion vector which is off from the motion pattern of the image classified by the motion-pattern classifying unit among the motion vectors in the plural pixel regions of the image, and estimates the newly-appearing rate using the motion vector other than the motion vector extracted by the off-pattern-vector extracting unit.

21. The image processing apparatus according to claim 6, wherein
the display-time calculating unit changes a calculation parameter when calculating a display time of the image based on the estimated newly-appearing rate according to the motion pattern of the image classified by the motion-pattern classifying unit.

22. The image processing apparatus according to claim 1, wherein the newly-appearing-rate estimating unit includes a motion-pattern classifying unit that classifies the motion pattern of an image as at least an image motion pattern of no-motion based on a motion vector calculated by the motion-vector calculating unit, and estimates the newly-appearing rate based on the motion pattern classified.

23. The image processing apparatus according to claim 22, wherein the motion-pattern classifying unit classifies the motion pattern of an image into the no-motion based on the size of the motion vector in the plural pixel regions.

24. The image processing apparatus according to claim 22, wherein the newly-appearing-rate estimating unit estimates the newly-appearing rate to be a possible minimum value when the motion pattern of an image is classified as the no-motion by the motion-pattern classifying unit.

25. The image processing apparatus according to claim 1, wherein the newly-appearing-rate estimating unit includes a motion-pattern classifying unit that classifies the motion pattern of an image as at least an image motion pattern of parallel movement based on a motion vector calculated by the motion-vector calculating unit, and estimates the newly-appearing rate based on the motion pattern classified.

26. The image processing apparatus according to claim 25, wherein the motion-pattern classifying unit classifies the motion pattern of an image as the parallel movement when fluctuation of an angle of a motion vector in the plural pixel regions of the image is equal to or smaller than a predetermined threshold.

27. The image processing apparatus according to claim 25, wherein the newly-appearing-rate estimating unit estimates the region which newly appears from the image edge when the motion pattern of an image is classified as the parallel movement by the motion-pattern classifying unit.

28. The image processing apparatus according to claim 1, wherein
the newly-appearing-rate estimating unit includes a motion-pattern classifying unit that classifies the motion pattern of an image as at least an image motion pattern of movement toward deeper side in depth direction based on a motion vector calculated by the motion-vector calculating unit, and estimates the newly-appearing rate based on the motion pattern classified.

29. The image processing apparatus according to claim 28 wherein the newly-appearing-rate estimating unit estimates the region which newly appears with reference to the advancing-direction position when the motion pattern of an image is classified as the movement toward deeper side in depth direction by the motion-pattern classifying unit.

30. The image processing apparatus according to claim 1, wherein
the newly-appearing-rate estimating unit includes a motion-pattern classifying unit that classifies the motion pattern of an image as at least an image motion pattern of movement toward front side in depth direction based on a motion vector calculated by the motion-vector calculating unit, and estimates the newly-appearing rate based on the motion pattern classified.

31. The image processing apparatus according to claim 30, wherein the newly-appearing-rate estimating unit estimates the region newly appeared from the image edge when the motion pattern of an image is classified as the movement toward front side in depth direction by the motion-pattern classifying unit.

32. The image processing apparatus according to claim 1, wherein
the newly-appearing-rate estimating unit includes a motion-pattern classifying unit that classifies the motion pattern of an image as at least an image motion pattern of scene change based on a motion vector calculated by the motion-vector calculating unit, and estimates the newly-appeared rate based on the motion pattern classified.

33. The image processing apparatus according to claim 32, wherein the newly-appearing-rate estimating unit estimates the newly-appearing rate to be a possible maximum value when the motion pattern of an image is classified into the scene change by the motion-pattern classifying unit.

34. An image processing method which processes time-series images picked up by an imaging device in time series, comprising:
calculating a motion vector between plural images constituting the time-series images with respect to plural pixel regions set in the image;
estimating a newly-appearing rate, which is a rate of a region newly appears in an image between the plural images, based on a motion vector calculated in the calculating; and
calculating a display time of the image according to the newly-appearing rate estimated in the estimating.

* * * * *